US012630822B2

(12) United States Patent
Thum et al.

(10) Patent No.: US 12,630,822 B2
(45) **Date of Patent: \*May 19, 2026**

(54) TREATMENT OF HEART FAILURE IN HUMAN SUBJECTS

(71) Applicant: Novo Nordisk A/S, Bagsvaerd (DK)

(72) Inventors: Thomas Thum, Hannover (DE); Claudia Ulbrich, Hannover (DE); Wilfried Hauke, Wiesbaden (DE); Steffen Rump, Sehnde (DE); Sandor Batkai, Hannover (DE)

(73) Assignee: Novo Nordisk A/S, Bagsvaerd (DK)

( * ) Notice: Subject to any disclaimer, the term of this patent is extended or adjusted under 35 U.S.C. 154(b) by 1168 days.

This patent is subject to a terminal disclaimer.

(21) Appl. No.: 17/618,801

(22) PCT Filed: Jun. 12, 2020

(86) PCT No.: PCT/EP2020/066273
§ 371 (c)(1),
(2) Date: Dec. 13, 2021

(87) PCT Pub. No.: WO2020/249713
PCT Pub. Date: Dec. 17, 2020

(65) Prior Publication Data
US 2022/0243204 A1      Aug. 4, 2022

(30) Foreign Application Priority Data

| | | |
|---|---|---|
| Jun. 14, 2019 | (EP) | 19180308 |
| Jan. 8, 2020 | (EP) | 20150700 |
| Mar. 10, 2020 | (EP) | 20162110 |
| May 18, 2020 | (EP) | 20175240 |

(51) Int. Cl.
*C12N 15/113* (2010.01)
*A61K 31/713* (2006.01)
*A61P 9/00* (2006.01)

(52) U.S. Cl.
CPC .......... *C12N 15/113* (2013.01); *A61K 31/713* (2013.01); *A61P 9/00* (2018.01); *C12N 2310/113* (2013.01); *C12N 2310/315* (2013.01); *C12N 2310/3231* (2013.01); *C12N 2310/344* (2013.01)

(58) Field of Classification Search
CPC ............ C12N 15/113; C12N 2310/113; C12N 2310/315; C12N 2310/3231; C12N 2310/344; A61K 31/713; A61P 9/00; A61P 9/04
See application file for complete search history.

(56) References Cited

U.S. PATENT DOCUMENTS

| | | | |
|---|---|---|---|
| 10,174,320 B2 * | 1/2019 | Soreq | A61P 1/16 |
| 2013/0150426 A1 | 6/2013 | Kossen et al. | |
| 2013/0289093 A1 | 10/2013 | Bhat et al. | |
| 2018/0119222 A1 | 5/2018 | Zou et al. | |

FOREIGN PATENT DOCUMENTS

| | | |
|---|---|---|
| CN | 103987858 A | 8/2014 |
| EA | 30211 A | 6/2015 |
| WO | 2013034653 A1 | 3/2013 |
| WO | 2016042561 A2 | 3/2016 |
| WO | 2019115788 A1 | 6/2019 |

OTHER PUBLICATIONS

Upadhyay et al. ("Emerging risk biomarkers in cardiovascular diseases and disorders." Journal of lipids 2015.1 (2015)).*
Zhou et al. ("miRNAS in cardiovascular diseases: potential biomarkers, therapeutic targets and challenges." Acta Pharmacologica Sinica 39.7 (2018): 1073-1084).*
Watts et al. ("Silencing disease genes in the laboratory and the clinic." The Journal of pathology 226.2 (2012): 365-379).*
Strukov et al., "Diseases of the Cardiovascular System", Litterra, 2010, 5th ed., p. 336.
Li et al., "Recent progress in understanding the role of microRNAs in hepatic stellate cell biology and liver fibrosis pathogenesis", J. Clin. Hepatol. May 2013, vol. 29, No. 5, pp. 385-388.
Vasyuk Yu. A. et al., "Modern possibilities and limitations of echocardiography in diseases of the cardiovascular system", Russian Journal of Cardiology, 2013, vol. 4, No. 102, pp. 28-32.
International Search Report and Written Opinion of PCT/EP2020/066273, Mailed Dec. 17, 2020, 11 pages.
R. Hinkel et al: "P5384 LNA-based mi R132 inhibition is cardioprotective in a pig model of percutaneous transverse aortic constriction (pTAC)", European Heart Journal, vol. 38, No. suppl 1, Aug. 29, 2017 (Aug. 29, 2017) XP055556356.
Ahmet Ucar et al: "The mi RNA-212/132 family regulates both cardiac hypertrophy and cardiomyocyte autophagy", Nature Communications, vol. 3, No. 1, Jan. 1, 2012 (Jan. 1, 2012), XP055471921.
Seema Dagwal et al: "microRNA Therapeutics in Cardiovascular Disease Models", Annual Review of Pharmacology and Toxicology, vol. 54, No. 1, Jan. 6, 2014 (Jan. 6, 2014), pp. 185-203. XP055449738.
Thomas Thum: "Facts and updates about cardiovascular non-coding RNAs in heart failure : Facts and updates RNAs", Esc Heart Failure, vol. 2, No. 3, Aug. 3, 2015 (Aug. 3, 2015), pp. 108-111, XP055413031.
Extended European Search Report for Application No. 19180308.9, dated Oct. 30, 2019, 10 pages.
International Preliminary Report on Patentability for PCT/EP2020/066273, mailed Dec. 14, 2021, 7 pages.
Masson et al: "Circulating microRNA-132 levels improve risk prediction for heart failure hospitalization in patients with chronic heart failure," European Journal of Heart Failure, vol. 20, 2018, pp. 78-85.

(Continued)

*Primary Examiner* — Kimberly Chong
(74) *Attorney, Agent, or Firm* — Elizabeth A. Dingess-Hammond

(57) ABSTRACT

The present invention refers to an oligonucleotide, which is an effective inhibitor of microRNA miR-132 and its use in medicine, particularly in the prevention or treatment of cardiac and/or fibrotic disorders of a human subject.

32 Claims, 33 Drawing Sheets

Specification includes a Sequence Listing.

(56)                   References Cited

OTHER PUBLICATIONS

Braunwald, Eugene: "The war against heart failure: the Lancet lecture," Nov. 16, 2014, http://dx.doi.org/10.1016/S0140-6736(14)61889-4. 13 pages.

He et al: "Risk Factors for Congestive Heart Failure in U.S. Men and Women," Arch Intern Med, Apr. 9, 2001, vol. 161, pp. 996-1002.

Weir et al: "Epidemiology of Heart Failure and Left Ventricular Systolic Dysfunction after Acute Myocardial Infarction: Prevalence, Clinical Characteristics, and Prognostic Importance," The American Journal of Cardiology, vol. 97, No. 10A, May 22, 2006, pp. 13F-25F.

Barry et al: "What causes a Broken Heart—Molecular Insights into Heart Failure," International Review of Cell and Molecular Biology, vol. 284, pp. 113-179.

Datta et al: "Cellular Survival: a play in three Akts," Genes & Development, vol. 13, pp. 2905-2927.

Debosch et al: "Insulin Signaling Pathways and Cardiac Growth," J Mol Cell Cardiol, May 2008, vol. 44, No. 5, pp. 855-864.

Frescas et al: "Nuclear Trapping of the Forkhead Transcription Factor Fox01 via Sirt-dependent Deacetylation Promotes Expression of Glucogenetic Genes," The Journal of Biological Chemistry, May 27, 2005, vol. 280, No. 21, pp. 20589-20595.

Glass, David J.: "PI3 Kinase Regulation of Skeletal Muscle Hypertrophy and Atrophy," Current Topics in Microbiology and Immunology, vol. 1, No. 346, pp. 267-278.

Gottlieb et al: "Mitochondrial turnover in the heart," Biochimica et Biophysica Acta 2011, vol. 1813, pp. 1295-1301.

Kolk et al: "LAD-Ligation: A Murine Model of Myocardial Infarction," Journal of Visualized Experiments, vol. 32, 2009, pp. 1-3.

McMullen et al: "The Insulin-like Growth Factor 1 Receptor Induces Physiological Heart Growth via the Phosphoinositide 3-Kinase(p110) Pathway," The Journal of Biological Chemistry, Feb. 6, 2004, vol. 279, No. 6, pp. 4782-4793.

Ni et al: "Foxo Transcription Factors Blunt Cardiac Hypertrophy by Inhibiting Calcineurin Signaling" Circulation, Sep. 12, 2016, pp. 1159-1168.

Ronnebaum et al: "The FoxO Family in Cardiac Function and Dysfunction," Annu Rev Physiol, Mar. 17, 2010, vol. 72, pp. 1-16.

Skurk et al: "The FOXO3a Transcription Factor Regulates Cardiac Myocyte Size Downstream of AKT Signaling," The Journal of Biological Chemistry, May 27, 2005, vol. 280, No. 21, pp. 20814-20823.

Grech et al: "Acute coronary syndrome: ST segment elevation myocardial infarction," BMJ, vol. 326, Jun. 21, 2003, pp. 1379-1381.

Ponikowski et al: "2016 ESC Guidelines for the diagnosis and treatment of acute and chronic heart failure," European Heart Journal, 2016, vol. 37, pp. 2129-2200.

Hill et al: "Cardiac Plasticity," The New England Journal of Medicine, 2008, vol. 358, pp. 1370-1380.

Lindow et al: "Discovering the first microRNA-targeted drug," J. Cell Biol., vol. 199, No. 3, pp. 407-412.

Spencer et al: "Heterogeneity in the Management and Outcomes of Patients with Acute Myocardial Infarction Complicated by Heart Failure," Circulation, Jun. 4, 2002, pp. 2605-2610.

Steg et al: "Determinants and Prognostic Impact of Heart Failure Complicating Acute Coronary Syndromes," Circulation 2004, vol. 109, pp. 494-499.

International Search Report for PCT/EP2020/066273, mailed Jul. 9, 2020, 5 pages.

* cited by examiner

■ LNA-scr
▨ CDR132L

Regional cardiac function, assessed by longitudinal strain rate (LSR)

<u>Cardiac segments:</u>
AB: anterior basal
AM: mid anterior
AA: anterior apex
PA: posterior apex
PM: mid posterior
PB: posterior basal Control
MI
MI+CDR132L Figure 9A
Figure 9B
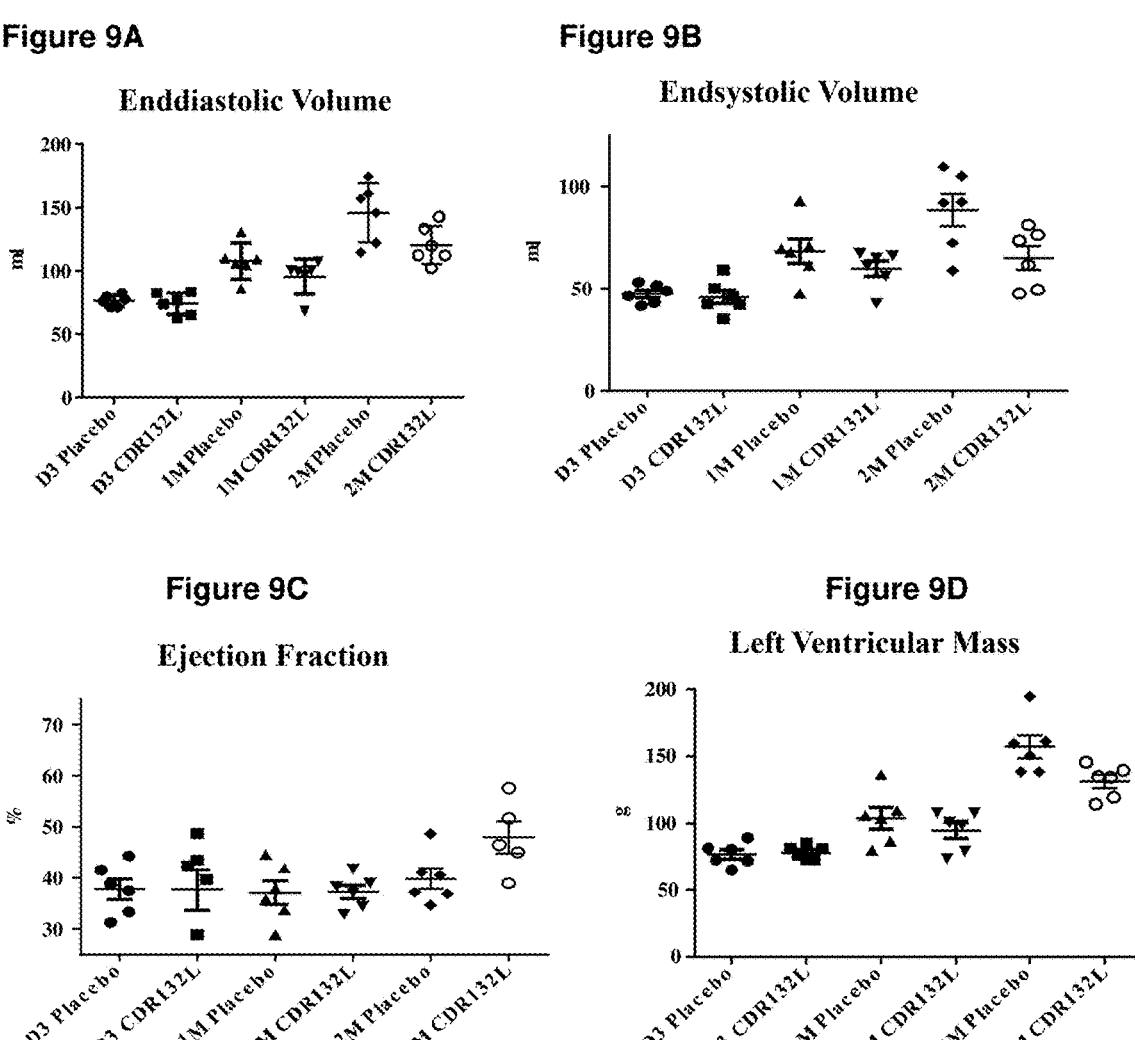
Figure 9C
Figure 9D
Figure 9E
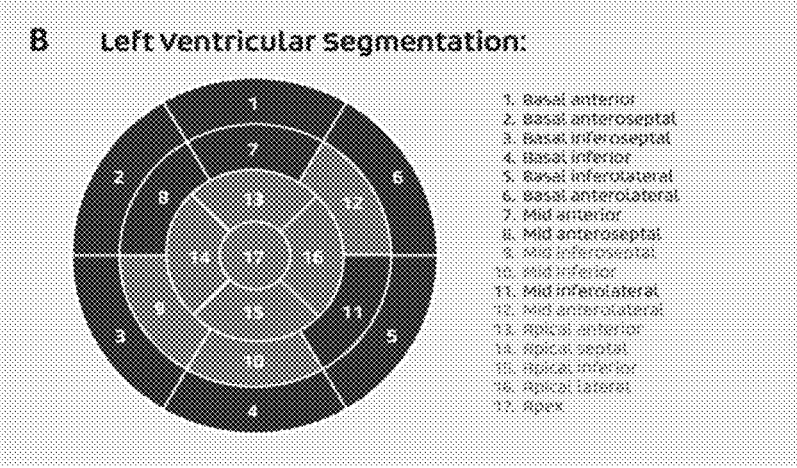

Control                    Placebo                    CDR132L

Cardiomyocyte Area

LNA-scr
■ CDR132L

TREATMENT OF HEART FAILURE IN HUMAN SUBJECTS

CROSS REFERENCE TO RELATED APPLICATIONS

This application is a National Phase Application of PCT/EP2020/066273, filed on Jun. 12, 2020, which claims the priority benefits of EP 20175240.9, filed on May 18, 2020, EP 20162110.9, filed on Mar. 10, 2020, EP 20150700.1, filed Jan. 8, 2020 and EP19180308.9, filed Jun. 14, 2019, the entire contents of which are incorporated by reference herein.

SEQUENCE LISTING

The instant application contains a Sequence Listing which has been submitted electronically in ASCII format and is hereby incorporated by reference in its entirety. Said ASCII copy, created on Apr. 6, 2020, is named SequenceListing.txt and is 3,091 bytes in size.

DESCRIPTION

The present invention refers to an oligonucleotide, which is an effective inhibitor of the microRNA miR-132, and its use in medicine, particularly in the prevention or treatment of cardiac disorders and/or fibrotic disorders in human subjects.

Heart failure is one of the leading pathological causes of mortality in the world. Myocardial infarction (MI) is the most important cause of heart failure as MI leads to subsequent progressive adverse remodeling of the heart resulting in heart failure with poor prognosis. The currently used therapeutic pharmacologic options for heart failure include angiotensin-modulating agents, β-blockers, diuretics, aldosterone antagonists, angiotensin-II-receptor blockers combined with neprilysin-inhibitors, vasodilators, inotropic agents, or SGLT-2 inhibitors. Although several clinical studies have shown significant decreases in heart failure-induced mortality rates for all these agents, the 5-year mortality rate remains unacceptably high at almost 50%. Thus, there is a great need to develop novel and more efficient therapeutic approaches for heart failure.

Pathological hypertrophic growth of cardiomyocytes can lead to the development of cardiac remodeling, heart failure and sudden cardiac death. Hypertrophic growth of cardiomyocytes is a response to increased cardiac wall stress caused by cardiac volume and/or pressure overload. Initially, cardiac hypertrophy is a compensatory mechanism aiming to decrease wall stress and to increase cardiac output. However, prolonged cardiac hypertrophy progresses to contractile dysfunction, cardiac decompensation and finally heart failure (Hill and Olson, 2008; Barry and Townsend, 2010). The transition from physiological to pathological hypertrophy can occur depending on many factors including myocyte loss through apoptosis or necrosis, alterations in autophagy, defects in contractile response, dysregulated calcium homeostasis, desensitization of adrenergic receptors, or cardiac fibrosis (Hill and Olson, 2008; Barry and Townsend, 2010). Hypertrophic signaling is largely mediated by the insulin signaling pathway (DeBosch and Muslin, 2008; Barry and Townsend, 2010). Both insulin and insulin-like growth factor-1 (IGF-1) activate pro-hypertrophic pathways in cardiomyocytes via the IGF-1 receptor, which activates the phosphoinositide-3-kinase (PI3K) (McMullen et al., 2004). PI3K activity leads to the activation of the serine/threonine kinase Akt via its phosphorylation and active Akt phosphorylates anti-hypertrophic FoxO transcription factors leading to their de-stabilization and prevention of nuclear localization (Datta et al., 1999; Skurk et al., 2005; Ronnebaum and Patterson, 2010). In contrast, acetylation of FoxO factors by sirtuin-1 (Sirt-1) leads to their stabilization and nuclear translocation (Frescas et al., 2005). Stabilized FoxO transcription factors are localized in the nucleus in order to regulate the expression of anti-hypertrophic genes. The anti-hypertrophic functions of FoxO proteins are largely mediated through suppression of the pro-hypertrophic calcineurin signaling pathway via the expression of anti-hypertrophic gene targets of FoxO factors, such as atrogin-1 (Ni et al., 2006; Ronnebaum and Patterson, 2010; Glas, 2010). Moreover, FoxO transcription factors also induce apoptosis and regulate autophagy in cardiomyocytes (Ronnebaum and Patterson, 2010).

MicroRNAs have been shown to have a key role in adverse cardiac remodeling. WO 2013/034653 describes that miR-132 and/or miR-212 may induce cardiac hypertrophy and thus constitute potential therapeutic targets for heart failure treatment.

WO 2016/042561 describes a method of treating a lipid-related disorder by administering to the subject a therapeutically effective amount of a polynucleotide agent which is substantially complementary to a nucleotide sequence of a human miR-132.

The present inventors have identified a novel oligonucleotide analogue which is an effective inhibitor of miR-132 expression in cardiomyocytes. The oligonucleotide analogue, in the following designated CDR132L, is a mixmer consisting of DNA and LNA building blocks, having internucleosidic phosphorothioate linkages.

Pre-clinical pharmacology studies were carried out with CDR132L in mice and pigs. In a transgenic mouse model of cardiac hypertrophy, CDR132L led to reverse cardiac remodeling associated with reduced expression of miR-132. In a mouse model of post-MI heart failure it was found that CDR132L treatment reduces post-MI left ventricular dysfunction and load independent parameters of systolic contractile function. Further, administration of CDR132L resulted in an improvement of cardiac function, and reduces miR-132 expression, cardiac stress signaling and post-MI hypertrophy.

In a pig model of post-MI heart failure CDR132L treatment was found to avert maladaptive remodeling and to improve left ventricular function. Further, CDR132L normalizes the tissue expression of pathologic heart failure markers such as BNP, ANP and provides a shift in myosin heavy change isoforms (MYH7/6 ratio). In pig models of post MI-heart failure, CDR132L was found to cure subacute and chronic heart failure.

CDR132L also lacks significant toxicity in a human liver cell line and isolated neonatal rat cardiomyocytes. By means of in vivo toxicity studies carried out in rats and minipigs it was found that the active agent was tolerated well even at high doses of 20 and 40 mg/kg, respectively.

Pharmacokinetic studies involving intravenous or subcutaneous administration of CDR132L to healthy rats and healthy pigs confirmed a dose-dependency of CDR132L tissue levels.

Further, it was shown that CDR132L exhibits superior effects compared to other oligonucleotide analogues having the same nucleotide sequence but a different distribution of LNA building blocks.

In an additional study, the present inventors have identified antifibrotic therapeutic effects for the oligonucleotide analogue CDR132L in an in vivo mouse model of myocardial infarction and in vitro models of liver fibrosis and lung fibrosis.

Furthermore, a significant relationship between the amount of miR-132 in circulating body fluids and the therapeutic efficacy of CDR132L was found. Thus, the amount of miR-132 in a body fluid is a relevant biomarker for therapy monitoring.

Based on the above results, a protocol of a clinical phase Ib study for administering CDR132L to human patients suffering from chronic heart failure has been developed. This clinical phase Ib study has meanwhile been successfully completed.

Thus, the oligonucleotide CDR132L is useful as an active agent in medicine, particularly in the prevention or treatment of cardiac disorders and/or fibrotic disorders.

BRIEF DESCRIPTION OF THE DRAWINGS

FIG. 1.

FIG. 2.

FIG. 3.

FIG. 5.

FIG. 7.

FIG. 9: FIGS. 9A, 9B, 9C, and 9D show that CDR132L treatment averts maladaptive remodeling and improves function, as determined by measurement of end diastolic volume, end systolic volume, ejection fraction and left ventricular function, respectively. FIG. 9E shows CDR132L treatment improves segmental contractility in segments corresponding to surviving/remote myocardium; cardiac MRI at endpoint.

FIG. 10.

FIG. 12.

FIG. 15.

FIG. 18.

Figure 1A:
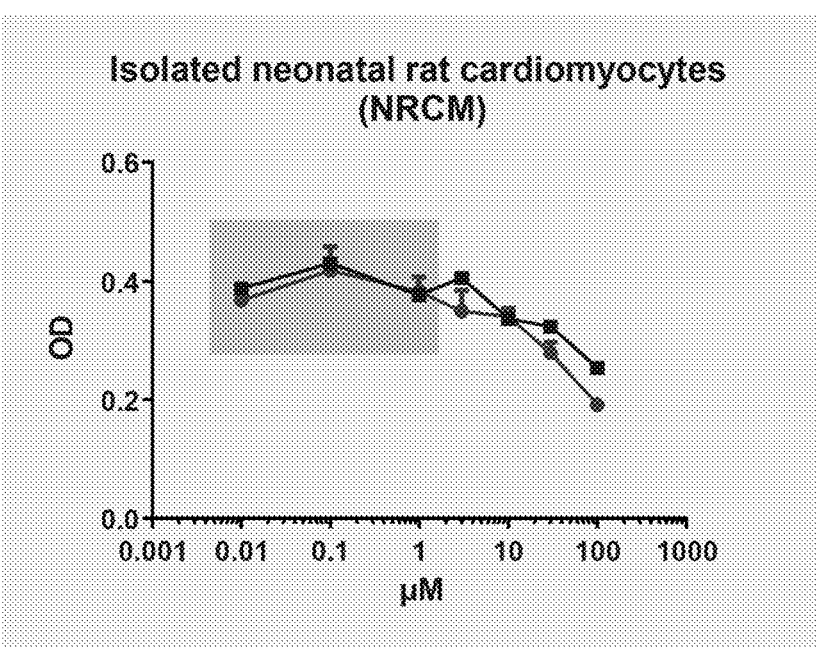
FIG. 1A shows the in vitro cytotoxicity comparison carried out in isolated neonatal rat cardiomyocytes (NRCM) for LNA-scr and CDR132L.

Accordingly, a first aspect of the present invention provides an oligonucleotide analogue, comprising a sequence of formula I:

$$5'-ATGGCTGTAGACTGTT-3'$$

wherein A, T, G and C are deoxyribonucleotide building blocks and wherein at least one G or T building block is a bridged nucleotide building block. This oligonucleotide is particularly suitable in the prevention and/or treatment of a disorder, more particularly a cardiac disorder in a human subject.

In a particular embodiment, the oligonucleotide comprises or has the sequence of formula II:

$$5'-A+TG+GC+TG+TA+GACTG+T+T-3'$$

wherein A, T, G and C are deoxyribonucleotide building blocks and wherein +G and +T are bridged nucleotide building blocks and/or morpholino nucleotide building blocks, particularly wherein +G and +T are LNA building blocks. This oligonucleotide is particularly suitable in the prevention or treatment of a disorder, more particularly of a cardiac or fibrotic disorder, in a human subject.

The oligonucleotide analogue of formula I or formula II may comprise at least one modified internucleosidic linkage, e.g. an internucleosidic linkage which is stabilized against nuclease digestion, e.g. a phosphorothioate or a phosphorodiamidate linkage. In specific embodiments, all internucleosidic linkages are modified linkages, particularly phosphorothioate linkages.

In a more specific embodiment, the invention relates to the oligonucleotide CDR132L as described herein.

The oligonucleotide CDR132L has a sequence of formula III:

$$5'-dA*+T*dG*+G*dC*+T*dG*+T*dA*+G*dA*dC*dT*dG*+T*+T-3'$$

wherein dA is 2'deoxyadenosine, dG is 2'deoxyguanosine, dC is 2'deoxycytidine and T is thymidine, wherein +T is an LNA-T building block and +G is an LNA-G building block and wherein * is a phosphorothioate linkage. This oligonucleotide is particularly suitable in the prevention or treatment of a disorder, more particularly of a cardiac or fibrotic disorder, in a human subject.

A further aspect of the present invention relates to a pharmaceutical composition comprising as an active agent an oligonucleotide analogue comprising a sequence of formula I, II or III and a pharmaceutically acceptable carrier, particularly for use in the prevention or treatment of a disorder, more particularly of a cardiac or fibrotic disorder, in a human subject.

As described above an oligonucleotide analogue comprising a sequence of formula I, II or III, is suitable for medical use.

In certain embodiments, the medical use relates to a use for the treatment or prevention of a disorder associated with, accompanied by and/or caused by pathological expression of miR-132. In certain embodiments, the medical use relates to the treatment or prevention of cardiac disorders, particularly cardiac hypertrophy-associated disorders. In certain embodiments, the medical use relates to the treatment of fibrotic disorders, e.g. disorders associated with, accompanied by and/or caused by pathological fibrosis, particularly cardiac fibrotic disorders, pulmonary fibrotic disorders or hepatic fibrotic disorders.

The oligonucleotide of formula I, II or III may consist of deoxyribonucleotide DNA building blocks and bridged nucleotide building blocks. A "bridged nucleotide" refers to a modified ribonucleotide wherein the ribose moiety comprises a two-or-three atom bridge connecting the 2'- and the 4'-carbon atom. For example, the bridge may comprise the structure 2'-O—$CH_2$-4', 2'-O—$CH_2$—$CH_2$-4', 2'-O—CH($CH_3$)-4' or a corresponding structure where O is replaced by S or NH. In a particular embodiment, the at least one bridged nucleotide building block is a locked nucleic acid (LNA) building block having a 2'-O—$CH_2$-4'-bridge.

The oligonucleotide of formula I, II or III has a length of at least 16 building blocks, e.g. a length of 16 to 20 building blocks. In a particular embodiment, the oligonucleotide of formula I, II or III has a length of 16 building blocks.

In some embodiments, the oligonucleotide of formula I, II or III comprises 5 to 10, e.g. 6 to 8, particularly, 7 bridged nucleotide building blocks, e.g. LNA building blocks.

In some embodiments, the oligonucleotide of formula I, II or III is a naked oligonucleotide. In some embodiments, the oligonucleotide may be conjugated to at least one heterologous moiety, e.g. a moiety, which does not contribute to the binding of the oligonucleotide to miR-132. The heterologous moiety may be a moiety, which improves targeting and/or cellular uptake, e.g. a lipid moiety such as cholesterol or a fatty acid, a saccharide or amino saccharide moiety such as an N-galactosamine containing moiety, a peptide or polypeptide moiety or a nucleosidic or nucleotidic moiety such as an aptamer. A heterologous moiety may be conjugated with the 5'- and/or 3'-terminus of the oligonucleotide analogue by means of covalent bond or a spacer.

The oligonucleotide of the present invention is suitable for use in medicine including human and veterinary medicine. In certain embodiments, the compound is useful in the prevention or treatment of a disorder associated with, accompanied by and/or caused by pathological expression, e.g. overexpression of miR-132. Administration of the compound was found to significantly reduce miR-132 expression in vitro and in vivo.

In some embodiments, the compound may be administered to patients showing an overexpression of miR-132 compared to healthy subjects. In some embodiments, the compound may be administered to patients not showing an overexpression of miR-132 compared to healthy subjects but still in need of a reduction of the level of miR-132.

The term "prevention" in the context of the present invention relates to the administration of the compound to a patient who is known to have an increased risk of developing a certain disorder. The term "treatment" in the context of the present invention relates to the administration of the compound to a patient, which has already developed signs and/or symptoms of a certain disorder. The term "patient" relates to a subject in need of administration of the compound of the invention in the field of human or veterinary medicine. In specific embodiments, the patient is a human patient.

In certain embodiments, the compound of the present invention is useful in the prevention or treatment of cardiac disorders, particularly of cardiac hypertrophy-associated disorders. For example, the compound is useful in the prevention or treatment of contractile dysfunction, cardiac decompensation, heart failure or for the prevention or treatment of cardiac remodeling after myocardial infarction, myocarditis, valvular heart diseases such as aortic stenosis or mitral valve insufficiency, genetic cardiac disorders with cardiac hypertrophy, e.g. hypertrophic non-obstructive and obstructive cardiomyopathy or Fabry disease. Further, the compound is useful in the prevention or treatment of cardiac fibrosis.

The compound is useful for administration to patients selected from (i) patients having an increased risk for developing heart failure, (ii) patients suffering from (congestive) heart failure, e.g. patients having an increased risk of heart failure progression, (iii) post-myocardial infarction patients and/or (iv) patients with congenital heart diseases associated with cardiac hypertrophy, such as aortic and/or pulmonal vein stenosis, atrial or ventricular septum defects.

In certain embodiments, the compound, particularly CDR132L, is useful for administration to human patients suffering from acute heart failure, to human patients suffering from subacute heart failure, or to human patients suffering from chronic and/or worsening chronic heart failure.

In certain embodiments, the compound, particularly CDR132L, is useful for administration to human patients suffering from stable heart failure, e.g. from stable heart failure of non-ischemic and/or ischemic origin.

In certain embodiments, the compound, particularly CDR132L, is useful for administration to human patients suffering from heart failure of non-ischemic and/or ischemic origin.

In certain embodiments, the compound, particularly CDR132L, is useful for administration to human patients suffering from a less advanced stage of heart failure or human patients suffering from an advanced stage of heart failure.

In certain embodiments, the compound, particularly CDR132L, is useful for administration to human patients suffering from heart failure stages I, II, III and/or IV according to the classification of the New York Heart Association (NYHA), for example, patients suffering from heart failure according to NYHA stages I and/or II, patients suffering from heart failure according to NYHA stages I, II and/or III or patients suffering from heart failure according to NYHA stages III and/or IV.

In certain embodiments, the compound, particularly CDR132L, is useful for administration to human patients suffering from heart failure and having an implanted pump, e.g. a left ventricular assisting device (LVAD).

In a particular embodiment, the compound is useful in preventing and/or treating left-sided heart failure including systolic heart failure, diastolic heart failure and a condition associated with systolic heart failure and/or diastolic heart failure.

Systolic heart failure is a type of heart failure associated with a reduced ejection fraction, particularly with an ejection fraction of 40% or less, wherein the left ventricle loses its ability to contract normally. Administration of the compound of the invention in the treatment of systolic heart failure may result in a stabilization, an increase and/or a normalization of the ejection fraction. The compound of the invention is suitable for administration to patients in risk for developing systolic dysfunction, e.g. patients suffering from hypertension, or blockages in coronary arteries.

Diastolic heart failure is a type of heart failure associated with impaired left ventricular relaxation with or without an increase of filling pressure. In many cases, diastolic heart failure is associated with a preserved ejection fraction. Administration of the compound of the invention in the treatment of diastolic heart failure may result in stabilization, improvement and/or normalization of left ventricular relaxation. The compound of the invention is suitable for administration to patients in risk for developing diastolic dysfunction, e.g. patients suffering from hypertension, hyperlipidemia, diabetes, obstructive sleep apnea, cardiac storage diseases, hereditary heart failure (e.g. mutations in titin or other structural genes).

In a further particular embodiment, the compound is useful in preventing and/or treating right-sided heart failure, particularly right-sided heart failure, which occurs as a result of left-sided heart failure.

In certain embodiments, the compound of the present invention is useful in the prevention or treatment of fibrotic disorders, particularly disorders associated with, accompanied by and/or caused by pathological fibrosis.

Pathological fibrosis is the formation of excess fibrous connective tissue in an organ or tissue, particularly associated with, accompanied by and/or caused by a pathological state. Pathological fibrosis can occur in many different organs and tissues within the body, typically as a result of inflammation or damage.

In a certain embodiment, the fibrosis is a cardiac fibrosis, e.g. a condition involving pathological fibrosis in the heart. Exemplary types of cardiac fibrosis include atrial fibrosis, endomyocardial fibrosis or fibrosis resulting from a previous myocardial infarction.

In a further embodiment, the fibrosis is a pulmonary fibrosis, e.g. a condition involving pathological fibrosis in the lung. Exemplary types of pulmonary fibrosis include fibrotic disorders caused by occupational or environmental factors, for example by exposure to toxins and pollutants such as silica dust, asbestos fibers, metal dust, coal dust, grain dust, bird and animal droppings. Other types of pulmonary fibrotic disorders are caused by radiation treatment and/or treatment with medicaments such as chemotherapeutic drugs, cardiac drugs, antibiotics or anti-inflammatory drugs. Still other types of pulmonary fibrotic disorders are caused by disorders including idiopathic pulmonary fibrosis, dermatitis, polymyositis, mixed connective tissue disease, an autoimmune disease such as rheumatoid arthritis, scleroderma, Sjogren's syndrome or systemic lupus erythematosus, sarcoidosis, pneumonia, a viral infection or gastroesophageal reflux disease (GERD).

In a further embodiment, the fibrosis may be hepatic fibrosis, e.g. a condition-involving pathological fibrosis in the liver. Exemplary types of hepatic fibrosis are caused by a viral infection, e.g. by hepatitis B and/or C virus, hereditary metabolic disorders, autoimmune hepatitis, biliary obstruction, iron overload, non-alcoholic fatty liver disease, including non-alcoholic fatty liver (NAFL) and non-alcoholic steatohepatitis (NASH) and alcohol liver disease.

In still further embodiments, the fibrosis may also be a vascular fibrosis, e.g. arterial stiffness, a cutaneous fibrosis, e.g. keloid formation or nephrogenic systemic fibrosis, an arthrofibrosis, some forms of adhesive capsulitis, soft tissue fibrosis such as mediastinal fibrosis or retroperitoneal fibrosis or bone marrow fibrosis such as myelofibrosis.

In certain embodiments, the invention encompasses determining the amount and/or activity of certain physiological parameters in the subject to be treated before, during and/or after administration of the compound of the invention. This concomitant diagnostic procedure may provide assistance for the medical use as described above. For example, the diagnostic procedure may provide assistance in risk assessment, patient stratification, monitoring of treatment course and/or post-treatment control.

In certain embodiments, the invention encompasses determining the amount and/or activity of miR-132 in the subject to be treated before, during and/or after administration of the compounds of the invention. In further embodiments, the invention encompasses determining the amount and/or activity of at least one marker particularly selected from cardiac markers and/or fibrotic markers. In certain embodiments, the invention encompasses determining the amount and/or activity of cardiac markers such as BNP e.g. NT-proBNP, ANP or myosin heavy change isoforms, e.g. the MYH7/6 ratio, and/or the levels of FoxO3 and/or SERCA2. In particular embodiments, the invention encompasses determining the amount of NT-proBNP. In still further embodiments, the invention encompasses determining the amount and/or activity of fibrotic markers such as collagen, e.g. collagen deposition and/or expression of fibrotic marker genes such as—but not limited to—collagen 1A1, collagen 1A2, collagen 3A1, procollagen type I C-terminal propeptide (PICP), and/or Galectin-3 (Gal-3), and/or a matrix metallopeptidase (metalloproteinase) such as Matrix Metalloproteinase 1 (MMP-1) and/or Matrix Metalloproteinase 2 (MMP-2).

The determination of the above parameters may be carried out in body fluid samples such as blood, plasma or serum or in tissue samples according to known methods at the nucleic acid and/or protein level and may provide useful diagnostic information, e.g. on the course of disease and/or course and/or success of the therapy.

Further, the inventors have found by means of PCR based detection method that the amount of miR132 in cardiac tissue shows a positive correlation with the amount of miR132 in a circulating body fluid, e.g. whole blood, plasma or serum. Thus, measurements of the amount of miR132 in a body fluid sample, e.g. a whole blood, plasma or serum sample provide an indication of the amount of miR132 in the target tissue, particularly in cardiac tissue.

In certain embodiments, the invention encompasses determining the amount and/or activity of miR-132 in the subject to be treated, e.g. a human subject, during the course of therapy. The term "course of therapy" in this context is to be understood as administration of a compound of the invention, particularly administration of CDR132L, to a subject in need thereof, particularly a human subject, over a certain time period, e.g. a time period of at least one day, at least one week, at least two weeks or at least on month. This determination can be carried out once or several times during the course of therapy. In particular embodiments, the amount of miR-132 is quantitatively determined in a sample from a body fluid, e.g. in sample from a circulating body fluid such as a blood, plasma or serum sample. Particularly, the sample is a plasma sample.

The amount and/or activity of miR-132 is inversely or negatively correlated to the concentration of the compound in the intended target organ, particularly the heart, but also to its activity and/or its therapeutic efficacy. Thus, the determination allows adjustment of the dose to be administered and/or adjustment of the interval between individual doses. Further, the determination allows stratification of patients with regard to their therapeutic response, for example, distinguishing responders from non-responders. In particular, the determination is carried out in patients with chronic disease, e.g. patients with chronic heart disease, several times during the course of therapy. For example, the determination may be carried in weekly, bi-weekly and/or monthly intervals.

In certain embodiments, the invention encompasses determining changes in ECG parameters during the course of therapy. The ECG parameters relevant for heart failure patients include but are not limited to measurement of QRS, T waves, left bundle branch block (LBBB) and/or right bundle branch block (RBBB); and/or R progression. Particularly relevant is the QRS measurement.

According to a further aspect of the invention, the oligonucleotide may be administered in a demand-based regimen, e.g. by adjusting the dose and/or the time interval between individual doses according to the measured amount of miR132 in a body fluid sample. For example, if the amount of miR132 in the body fluid sample is found to be above a predetermined value, a new dose of the oligonucleotide is administered.

Thus, the present invention relates to the oligonucleotide as described above for use in the prevention or treatment of a cardiac disorder in a human subject, wherein the oligonucleotide is administered by a demand-based regimen, particularly comprising the steps:

(i) measuring the amount of miR132 in a body fluid sample, e.g. in a whole blood, serum or plasma sample, of a subject being treated with the oligonucleotide, (ii) administering the oligonucleotide in a dose and/or time interval between individual doses as determined according to the measured amount of miR132 in step (i), particularly wherein a new dose of the oligonucleotide is administered if the amount of miR132 in the body fluid sample is found to be above a predetermined value, e.g. the baseline value.

The compound of the invention may be administered as a pharmaceutical composition comprising a pharmacologically acceptable carrier. Administration may be carried out by known methods, wherein the compound is introduced into the desired target cell or organ of the subject to be treated.

The compound may be administered as such or as a conjugate with a heterologous moiety as described above.

For pharmaceutical applications, the composition may be in the form of a solution, e.g. an injectable solution, emulsion, suspension or the like.

The composition may be administered in any suitable way, e.g. parenterally, in particular by injection such as subcutaneous, intramuscular, intravenous or intra-arterial injection, or infusion, by oral or inhalative intake and/or by dermal application, or by local application to the target organ, e.g. by intracoronary perfusion. The carrier may be any suitable pharmaceutical carrier. Preferably, a carrier is used which is capable of increasing the efficacy of oligonucleotide molecules to enter the target cells. Suitable examples of such carriers are liposomes, e.g. cationic liposomes, or predesigned exosomes.

In certain embodiments, the compound, particularly CDR132L, is administered by intravenous injection or by subcutaneous injection.

The compound is administered in a pharmaceutically effective dosage depending on the route of administration and the type or severity of the disease.

In certain embodiments, the compound is administered to a human subject in a dose of about 0.1-100 mg/kg body weight per application, e.g. about 0.2-50 mg/kg body weight, about 0.8-20 mg/kg body weight per application, or about 3-10 mg/kg body weight per application, for example, by parenteral application, particularly by injection or infusion, e.g. by intravenous injection or by subcutaneous injection.

In a pharmacokinetic study it was found that the compound had a long half-life time of about three weeks in cardiac tissue and a short bi-phasic half-life time in plasma. These results demonstrate that the compound is suitable in a variety of different treatment regimens, e.g. in a treatment regimen comprising applications in time intervals of less than a week and in a treatment regimen comprising applications in time intervals of a week or longer.

In certain embodiments, the oligonucleotide is administered to a human subject in a regimen selected from daily administration, administration each second day, administration each third day, and administration each fourth day, particularly wherein the oligonucleotide is administered parenterally, more particularly by intravenous or subcutaneous injection, e.g. subcutaneous self-injection by the patient.

In these embodiments, the oligonucleotide may be administered in a body weight dependent dose and/or in a fixed dose. For example, the oligonucleotide may be administered in a dose of 0.01 mg/kg body weight to 50 mg/kg body weight, in a dose of 0.02 mg/kg body weight to 10 mg/kg body weight or in a dose of 0.05 mg/kg body weight to 5 mg/kg body weight per application. Alternatively, the oligonucleotide may be administered in a fixed dose of 1 mg to 5000 mg, in a fixed dose of 2 mg to 1000 mg, or in a fixed dose of 5 mg to 500 mg per application.

In still further embodiments, the oligonucleotide is administered to a human subject in a regimen selected from weekly administration, administration each second week, administration each third week, administration each fourth week or each month, administration each sixth week, administration each second month, administration each third month, administration each sixth month, and administration once per year, particularly wherein the oligonucleotide is administered parenterally, more particularly by intravenous or subcutaneous injection, e.g. subcutaneous self-injection by the patient.

In these embodiments, the oligonucleotide may be administered in a body weight dependent dose or in a fixed dose. For example, the oligonucleotide may be administered in a dose of 0.01 mg/kg body weight to 50 mg/kg body weight, in a dose of 0.05 mg/kg body weight to 20 mg/kg body weight or in a dose of 0.1 mg/kg body weight to 10 mg/kg body weight per application. Alternatively, the oligonucleotide may be administered in a fixed dose of 1 mg to 5000 mg, in a fixed dose of 5 mg to 2000 mg, or in a fixed dose of 10 mg to 1000 mg per application.

In still further embodiments, the compound may be administered to a human patient in a starting dose, e.g. 1 or 2 starting doses, and subsequently in at least one maintenance dose, which is different from the starting dose. For example, the starting dose may be higher than the maintenance dose, such as about 1.5-3 times, e.g. about 2 times as high as the maintenance dose. The starting dose and/or the maintenance dose may be administered as a body weight dependent dose or in a fixed dose. In specific embodiments, the starting dose is about 3-10 mg/kg, and the maintenance dose is about 1-7.5 mg/kg. Additionally, a maintenance dose may be adjusted, e.g. by titration, based on the amount of miR132 in body fluids such as blood, plasma or serum.

In a human clinical phase Ib study, the compound was found to demonstrate excellent tolerability and safety in human patients with heart failure in dose escalating single and repeat doses on top of standard of care. The pharmacokinetic profile shows no signs for accumulation and high level of dose linearity. Its unique mode of action in heart failure was confirmed in relevant pharmacodynamic parameters and target engagement. No serious adverse events and no injection site reactions were observed and no patient withdrew from the study because of adverse events. The compound was well tolerated and did not show any signs of toxicity in doses up to 10 mg/kg.

The compound may be administered as a monotherapy or in combination with a further different medicament, particularly a medicament suitable for the prevention or treatment of cardiac disorders or fibrotic disorders as described above.

Examples of further medicaments suitable for the prevention or treatment of cardiac disorders are angiotensin-modulating agents, β-blockers, diuretics, aldosterone antagonists, vasodilators, ionotrophic agents, statins, neprilysin-inhibitors, or SGLT-2 inhibitors or combinations thereof, e.g. a combination of a neprilysin-inhibitor, e.g. sacubitril, with an angiotensin-II-receptor blocker, e.g. valsartan.

In certain embodiments, the compound is administered together with (i) at least one diuretic, (ii) at least one angiotensin-converting enzyme inhibitor, (iii) at least one β-blocker, optionally (iv) an angiotensin-II-receptor blocker and/or (v) optionally an If-channel inhibitor such as ivabradine and optionally (vi) an angiotensin-receptor-neprilysininhibitor, and optionally (vii) an glucose Co-transporter 2 inhibitor such as empagliflozin and dapagliflozin, and/or optionally (viii) stem cell therapeutics and/or optionally (ix) anti-miRNAs targeting different pathways and/or optionally (x) a SGLT-2 inhibitor. Suitable inhibitors, stem cell therapeutics and/or mi-RNAs targeting different pathways can be selected by the person skilled in the art. The compounds and inhibitors according to (i)-(x) can be independently selected and combined in any suitable manner.

Examples of further medicaments suitable for the prevention of treatment of fibrotic disorders are medicaments for the prevention or treatment of cardiac fibrosis such as ACE inhibitors, e.g. lisinopril, Angiotensin II receptor blockers, e.g. candesartan, losartan or olmesartan, aldosteron antagonists, e.g. spironolactone and/or TGF β inhibitors, e.g. pirfenidone or tranilast, medicaments for the prevention or treatment of pulmonary fibrosis such as anti-fibrotic agents, e.g. nintedanib or pirfenidone, anti-inflammatory agents, e.g. corticosteroids, azathioprine, cyclophosphamide and mycophenolate mofetil, anti-reflux agents, e.g. protein pump inhibitors or $H_2$ blockers and/or anti-coughing agents and medicaments for the prevention and/or treatment of hepatic fibrosis such as ACE inhibitors, e.g. benazepril, lisinopril or ramipril, antiviral agents or PPAR α-agonists.

Still further, the invention relates to the use of a compound of the invention as described herein above for the manufacture of a medicament for the prevention or treatment of a cardiac disorder.

Still further, the invention relates to the use of a compound of the invention as described herein above for the manufacture of a medicament for the prevention or treatment of a fibrotic disorder.

Still further, the invention relates to a method for the prevention or treatment of a cardiac disorder comprising administering to a subject in need thereof a therapeutically effective amount of at least one compound as described herein.

Still further, the invention relates to a method for the prevention or treatment of a fibrotic disorder comprising administering to a subject in need thereof a therapeutically effective amount of at least one compound as described herein.

Still further, the invention relates to a kit for monitoring therapy with an oligonucleotide as described above comprising determining the amount and/or activity of miR-132 from a subject to whom the oligonucleotide has been administered. The kit may comprise a primer binding to miR-132 coding DNA or DNA which is complementary thereto, preferably primer has-miR-132, a primer binding to miR-39 coding DNA or DNA which is complementary thereto, preferably primer cel-miR-39 and optionally a positive control hsa-miR-132 and optionally a positive control cel-miR-39. According to a preferred embodiment, primers hsa-miR-132 and miR-39 are used together. Further, the kit can comprise additional compounds, e.g. a qPCR Mastermix and nuclease-free water. In a preferred embodiment, the kit comprises the primer hsa-miR-132, primer cel-miR-39 the positive controls cited above and qPCR Mastermix and nuclease free water. Suitable primers can be selected by the person skilled in the art.

Further, the present invention shall be described in more detail by the following Figures and Examples.

Example 1—Silencing of miR-132 Expression in Cardiomyocytes

A quantitative in vitro assay for miRNA inhibitory activity of numerous structure analogue compounds derived form an anti-miR-132 library was carried out. Silencing of miRNA expression was quantified by a TaqMan® assays and quantitative real-time PCR.

The study was conducted in isolated rat cardiomyocytes after hypertrophic stimulation by phenylephrine/isoproterenol treatment in concentrations of 10 μM. Cells were incubated for 48 hours in standard cell culture medium. Test compounds were administered individually in a concentration of 100 nM. Tests were carried out in triplicates.

The compound CDR132L, an LNA-DNA mixmer having a phosphorothioate backbone, was identified as most potent compound from the anti-miR-132 structure analogue library.

The structure of CDR132L is as follows:

$$5'-dA*+T*dG*+G*dC*+T*dG*+rdA*+G*dA*dC*dT*dG*+T*+$$

$$T-3'$$

wherein dA is 2'deoxyadenosine, dG is 2'deoxyguanosine, dC is 2'deoxycytidine and T is thymidine, wherein +T is an LNA-T building block and +G is an LNA-G building block and wherein * is a phosphorothioate linkage.

Example 2—Toxicology Profiling 2.1 Study Aim: Toxicity Profiling of CDR132L 2.2 Study Outline:

An in vitro cytotoxicity assay was carried out in human liver cell cells (HepG2) and isolated neonatal cardiomyocytes (NRCM). A colorimetric commercial MTT assay was used to assess cytotoxicity. After addition of individual compounds, cells were incubated in DMEM medium for 48 h. The effect of CDR132L (red) was compared to a scrambled LNA oligonucleotide, used as control (blue) in a dose range of 0.01-100 μM. The therapeutic dose range is marked in grey.

Figure 1B:
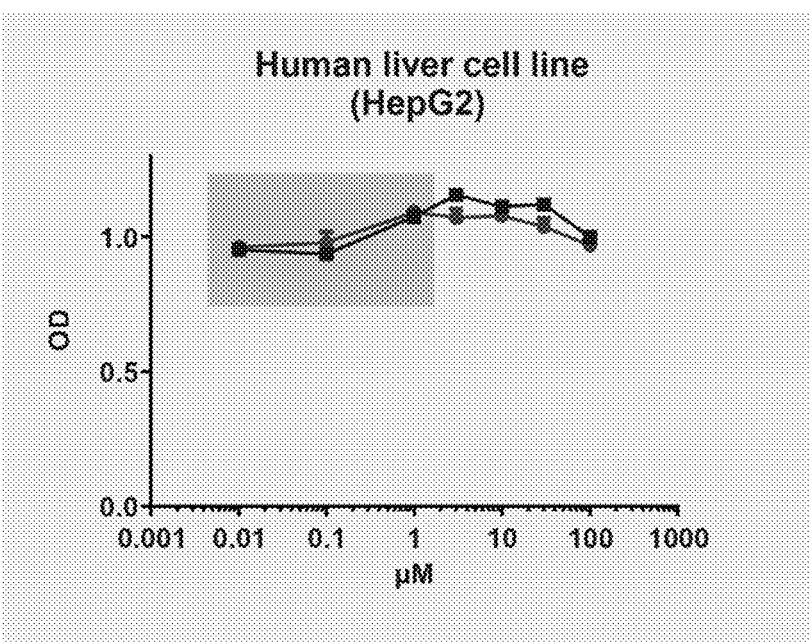
FIG. 1B shows the in vitro cytotoxicity comparison of human liver cell line (HepG2) for LNA-scr and CDR132L.

2.3 Results:

No significant toxicity of CDR132L in HepG2 cells and NRCM was found over the therapeutic dose range (cf. FIGS. 1A and 1B).

Example 3—Left Ventricular Reverse Remodeling of the Failing Heart by Administration of CDR132L in a Transgenic Mouse Model 3.1 Study Aim:

Test efficacy of CDR132L in reversing heart failure in a mouse model of heart failure.

3.2 Study Outline:

Model of cardiac hypertrophy: Transgenic (TG) mice with cardiac miR-132 overexpression (Ucar et al. 2012).

Figure 2A:
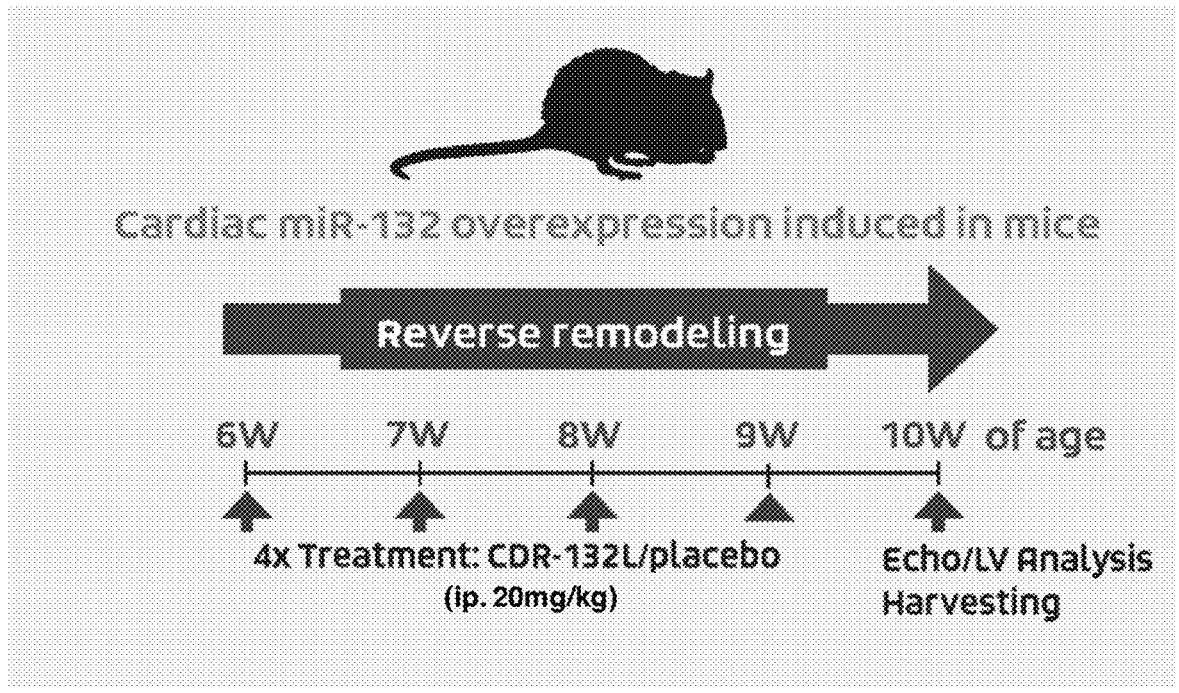
FIG. 2A illustrates the study outline for reverse remodeling of cardiac microRNA-132 (miR-132) overexpression induced in mice.

Treatment: weekly 20 mg/kg ip. CDR132L or placebo (cf. FIG. 2A)

Groups: wild type (WT) littermate+placebo, WT+CDR132L, TG+placebo, TG+CDR132L. n=6/group.

Figure 2B:
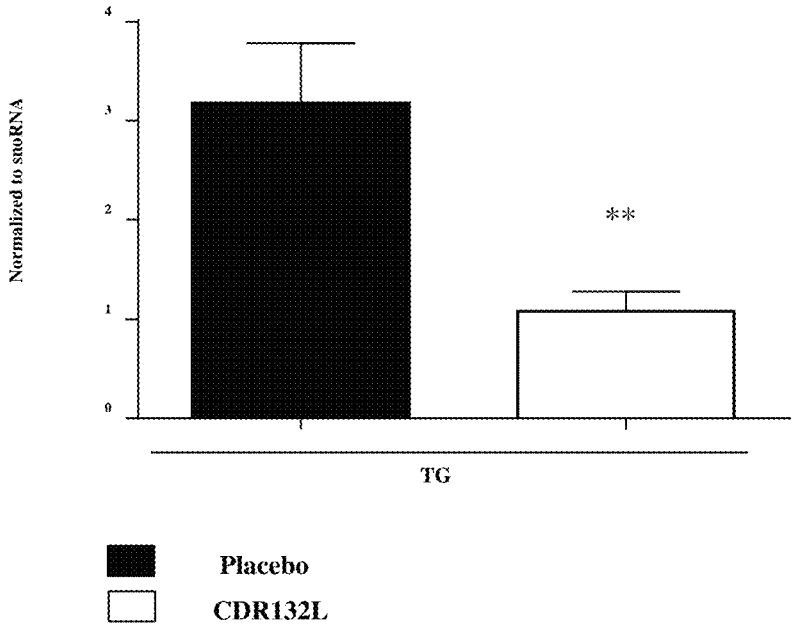
FIG. 2B illustrates the expression of miR-132 for CDR132L versus placebo.

Expression levels of miR-132 were detected via qPCR. Statistical test: unpaired t-test. (FIG. 2B).

** $p<0.01$, n=6/group.

Figure 3A:
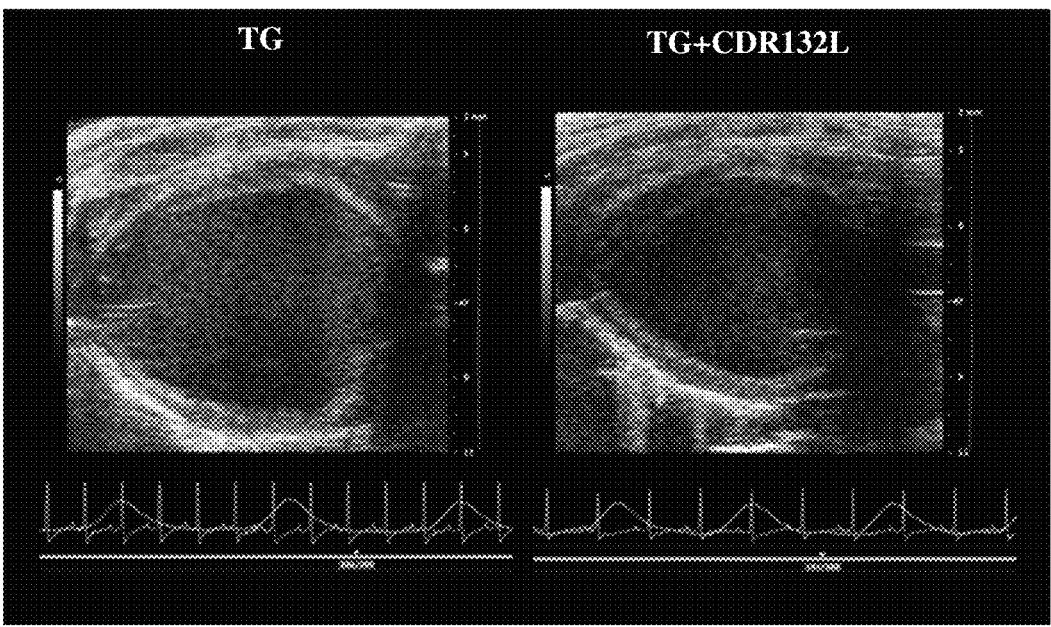
FIG. 3A shows representative echocardiography images of the heart in transgenic (TG) mice and TG+CDR132L group.

3.3 Results:

Representative echocardiography images of the heart (FIG. 3A).

Figure 3B:
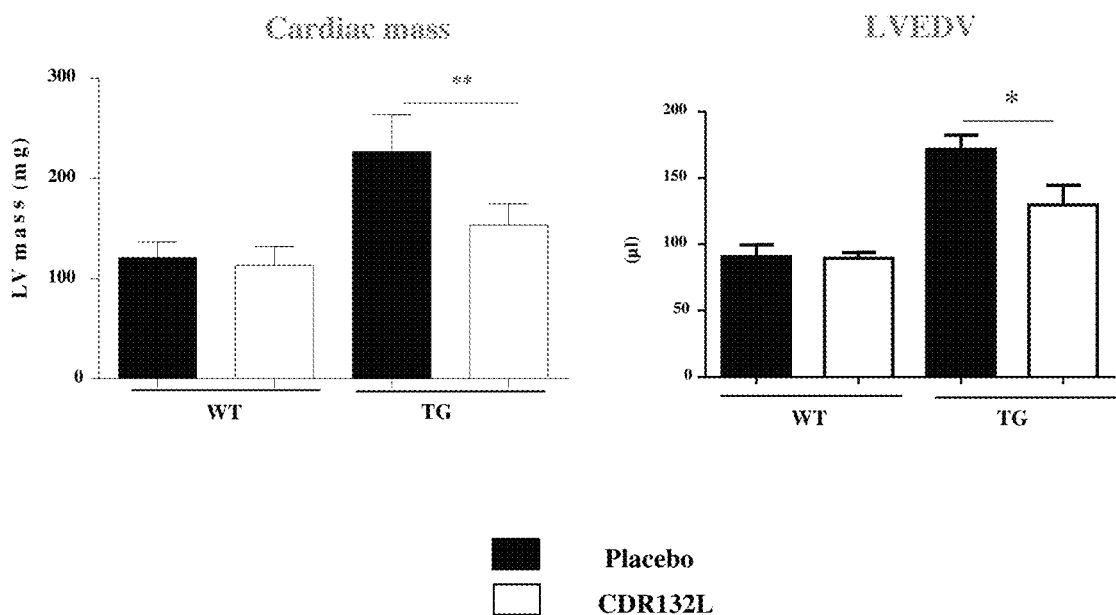
FIG. 3B shows that CDR132L reverses hypertropy as measured by cardiac mass and end diastolic volume (LVEDV).

CDR132L reverses hypertrophy as measured by cardiac mass and end diastolic volume (LVEDV) (FIG. 3B).

Figure 3C:
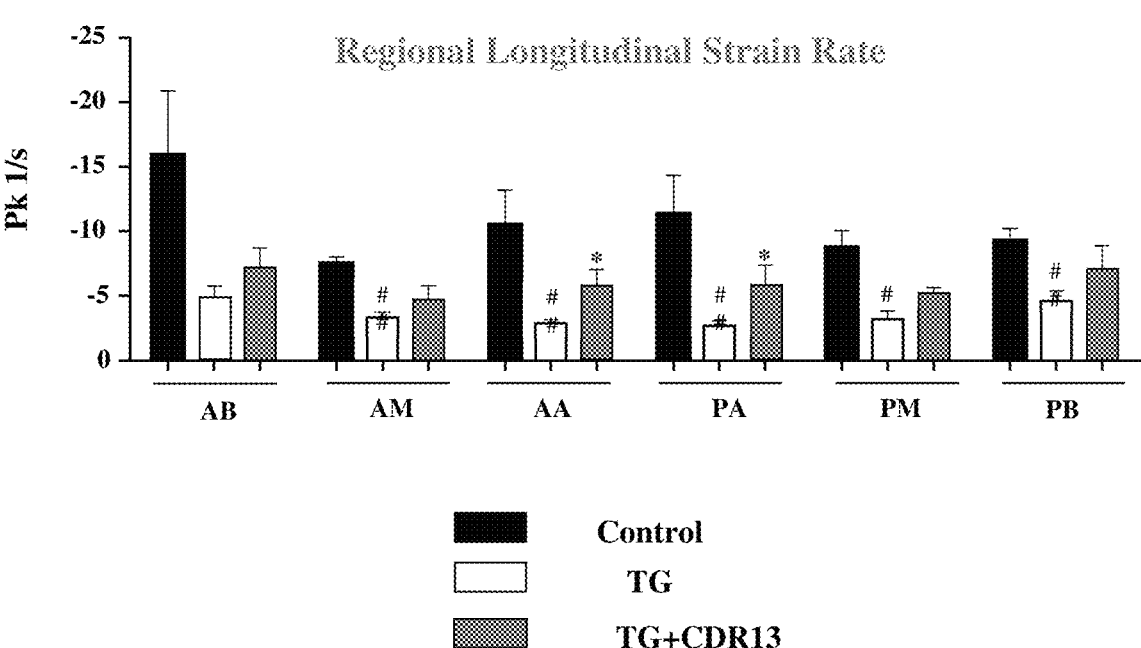
FIG. 3C shows that CDR132L improves regional contractile function in most segments of the left ventricle.

CDR132L improves regional contractile function in most segments of the left ventricle (AB, anterior basal; AM, mid anterior; AA, anterior apex; PA posterior apex; PM, mid posterior and PB, posterior basal) (FIG. 3C).

Figure 4:
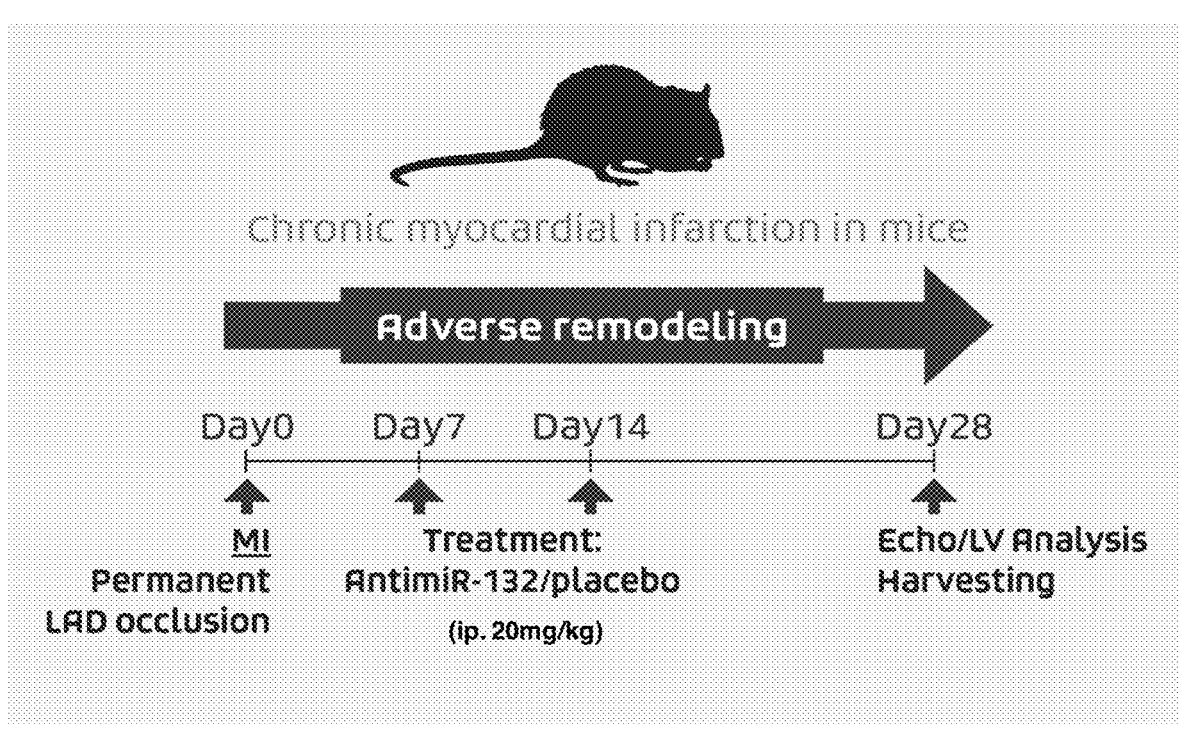
FIG. 4 illustrates the study outline for adverse remodeling of chronic myocardial infarction in mice.
Figure 5A:
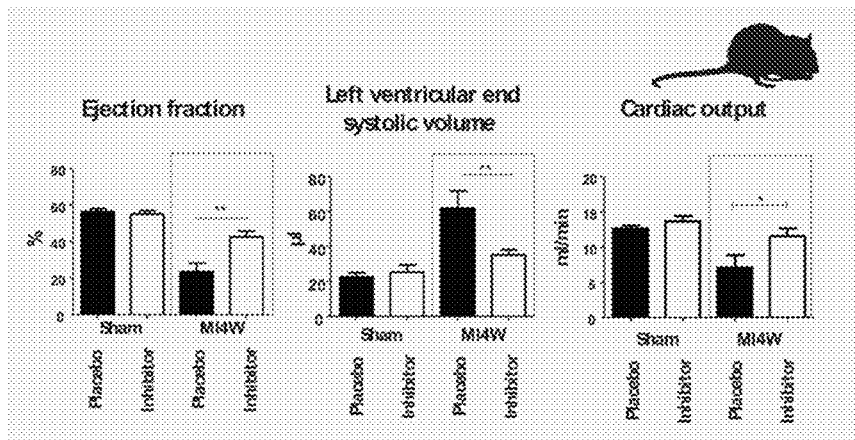
FIG. 5a shows CDR132L treatment improves post-MI left ventricular dysfunction.
Figure 5B:
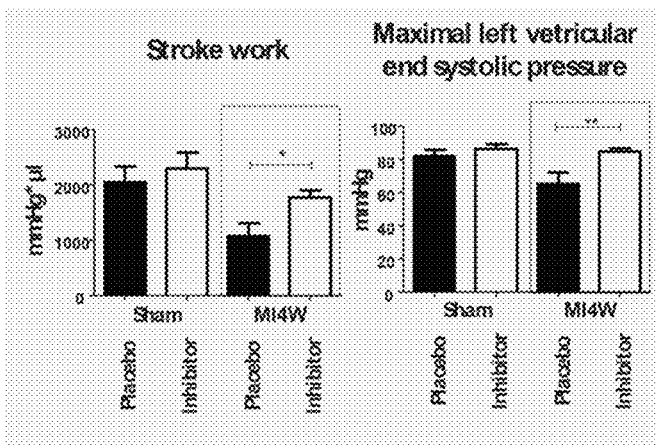
FIG. 5B shows that load independent parameters of systolic contractile function were also improved.
Figure 5C:
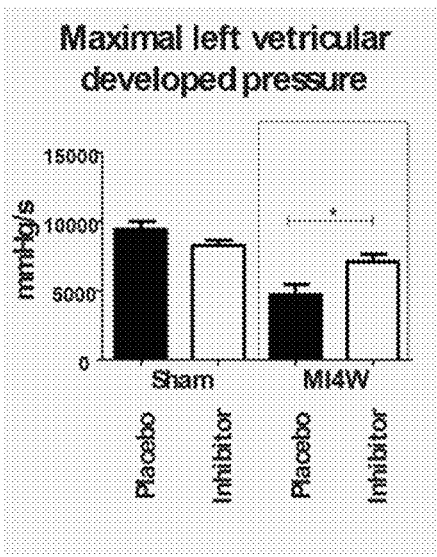
FIG. 5C shows maximal left ventricular developed pressure.
Figure 6:
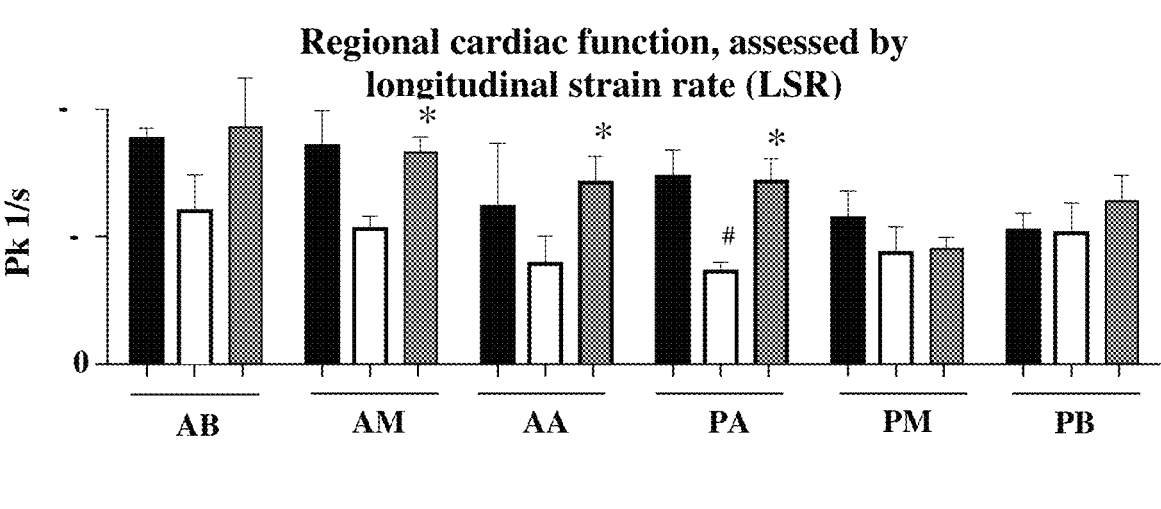
FIG. 6 illustrates CDR132L treatment improves longitudinal strain rate (LSR) and thus reverses the post-MI contractile dysfunction in individual cardiac segments in the remote area of the heart.
Figure 6:
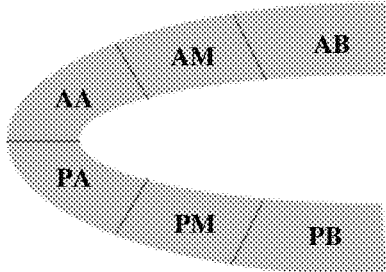
Figure 6:
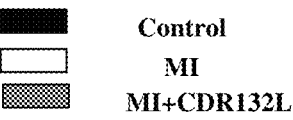
Figure 7A:
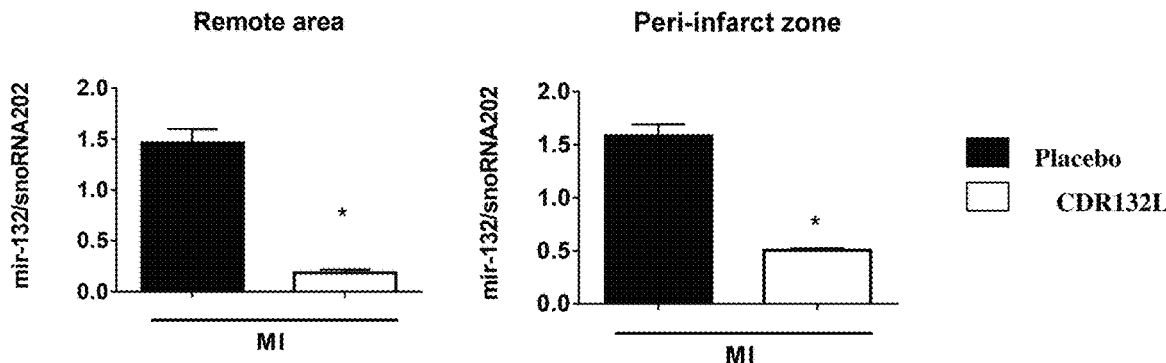
FIG. 7A shows that CDR123L treatment effectively silences miR-132 expression in cardiac tissues, in e.g. remote (non-infarct) area and peri-infarct zone.
Figure 7B:
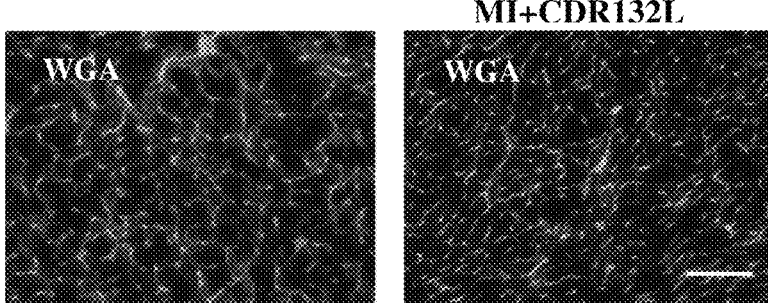
FIG. 7B shows that at histological level, CDR132L reduces cardiomyocyte size in remote area of the post-MI heart.
Figure 7C:
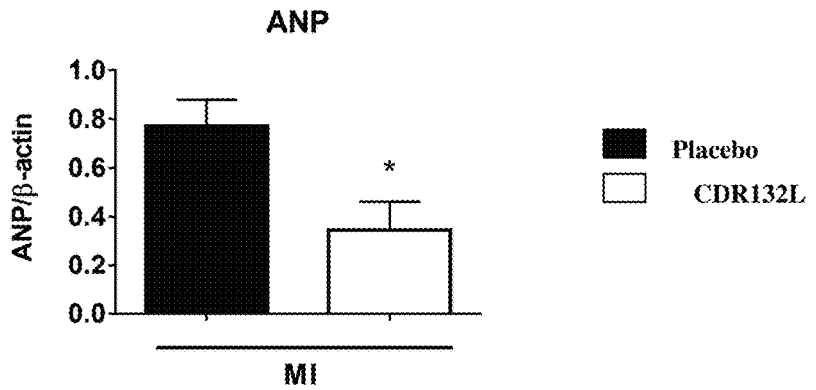
FIG. 7C shows that at tissue level, CDR132L reduces the expression of the cardiac stress signal ANP in the post-MI heart.

Example 4-Administration of CDR132L in a Mouse Model of Post-MI Heart Failure 4.1 Study Aim:
  Test efficacy of CDR132L in a mouse model of post-MI heart failure
4.2 Study Outline:
  Mouse model of myocardial infarction (MI): permanent ligation of coronary artery (LAD) in C57BL/6N mice (Kolk et al., 2009).
  Groups: MI or sham, treated with CDR132L or placebo
  Treatment: 20 mg/kg ip, on day 7 and 14 post-MI
  Endpoint: LV function at day 28 post-MI. n=6-7/group. (FIG. 4),
4.3 Results:
  CDR132L treatment improves post-MI left ventricular dysfunction (FIG. 5A). Load independent parameters of systolic contractile function were also improved (FIG. 5B) (*p<0.05).
  CDR132L treatment also improves longitudinal strain rate (LSR) and thus reverses the post-MI contractile dysfunction in individual cardiac segments in the remote area of the heart. (*p<0.05) (FIG. 6).
  CDR123L treatment effectively silences miR-132 expression in cardiac tissues, in e.g. remote (non-infarct) area and peri-infarct zone (FIG. 7A).
  At histological level, CDR132L reduces cardiomyocyte size in remote area of the post-MI heart (FIG. 7B).
  At tissue level, CDR132L reduces the expression of the cardiac stress signal ANP in the post-MI heart (FIG. 7C).

Figure 8:
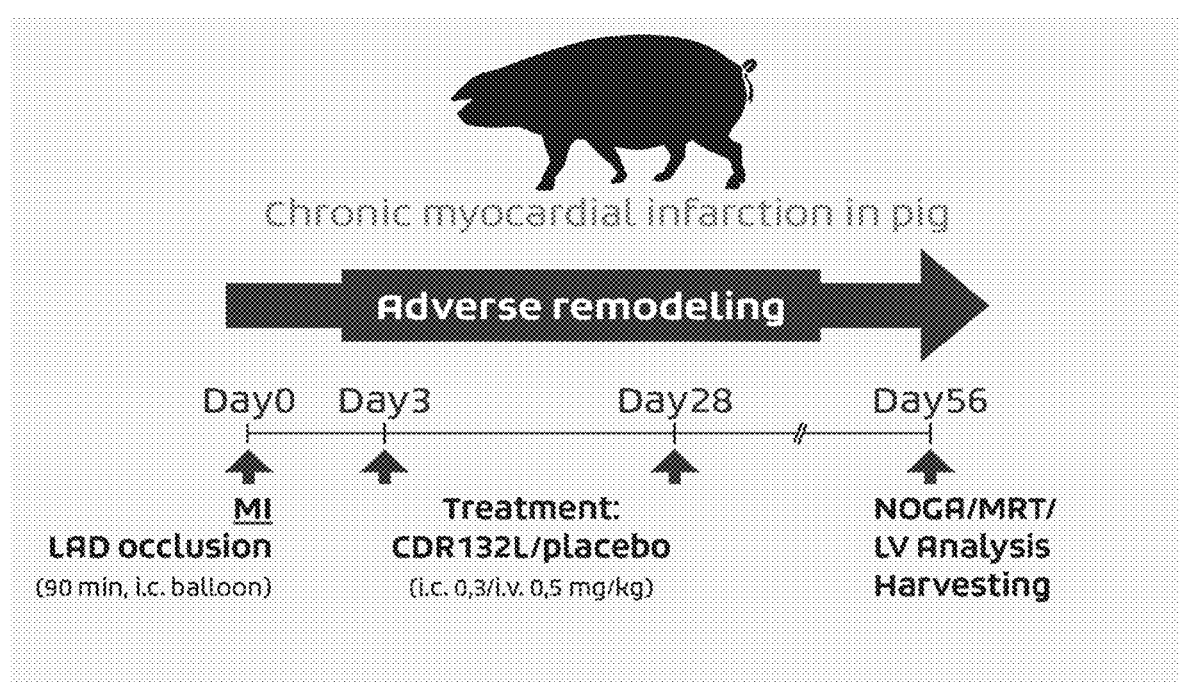
FIG. 8 illustrates the study outline for adverse remodeling of chronic myocardial infarction in pig.
Figure 10A:
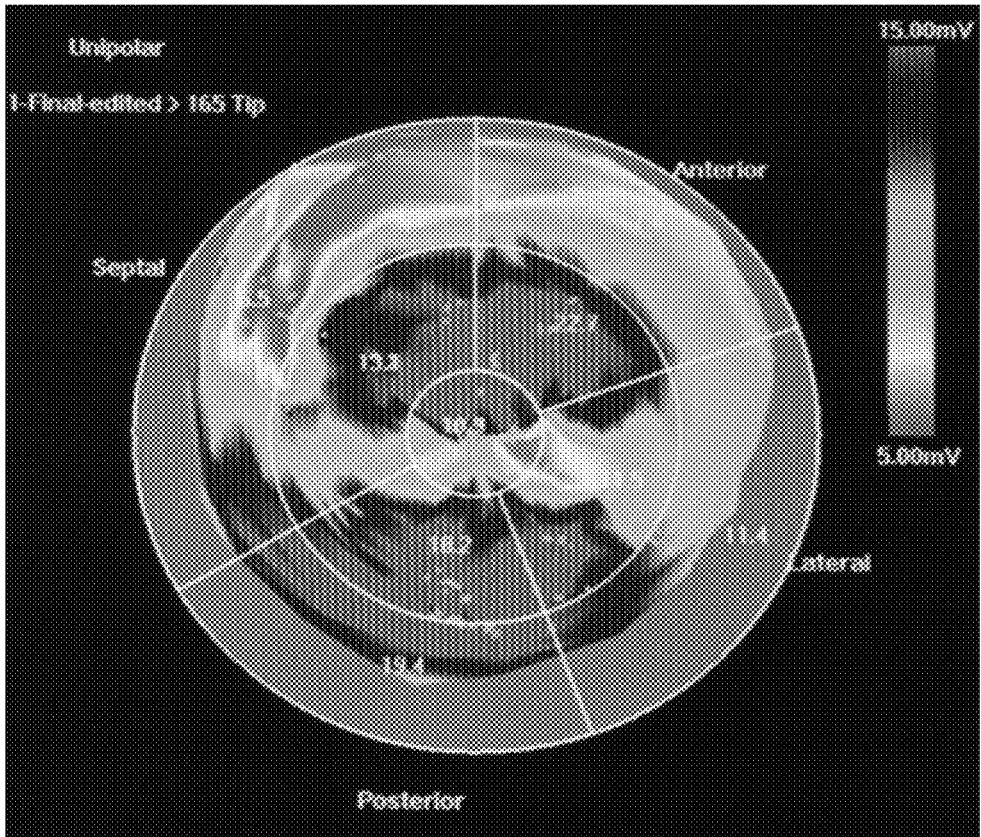
FIGS. 10A and 10B shows that CDR132L treatment averts maladaptive remodeling and improves LV viability in the apical area as determined by NOGA, electro-anatomical mapping at endpoint: n=6/group and via cardiac vitality (placebo vs CDR132L), respectively.
Figure 10B:
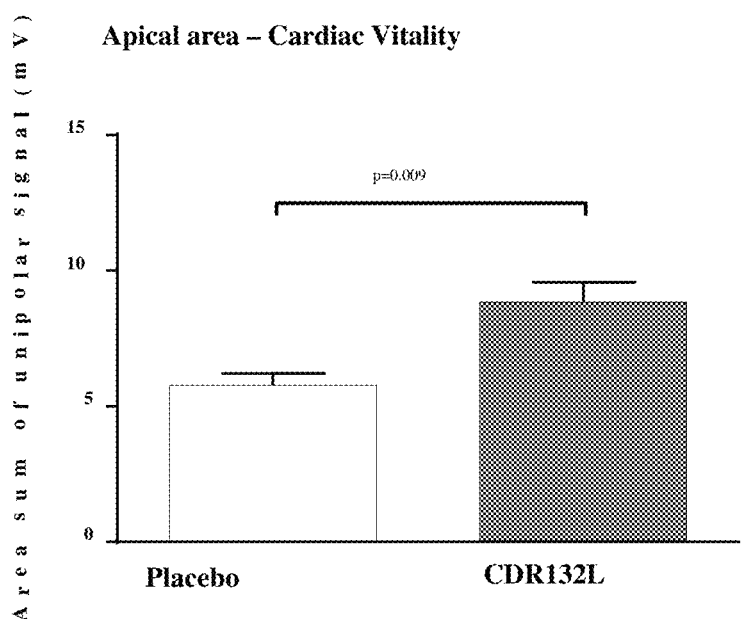
Figure 11:
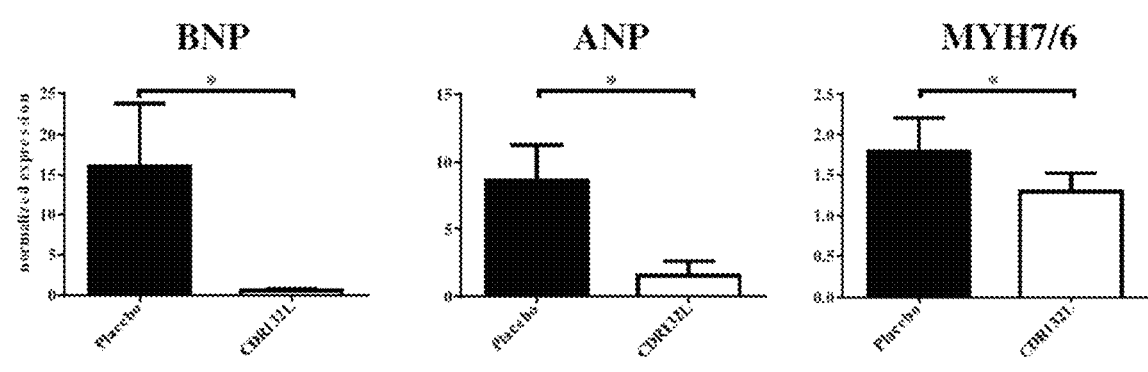
FIG. 11 shows that CDR132L normalizes the tissue expression of pathologic heart failure markers in ANP and BNP and provides a shift in myosin heavy change isoforms, i.e. MYH7/6 ratio.

Example 5-Test of CDR132L in a Pig Model of Post-MI Heart Failure 5.1 Study Aim:
  Proof of in vivo efficacy of CDR132L in a clinically relevant model of post-myocardial infarction.
5.2 Study Setup:
  Pig model of myocardial infarction elicited by 90 min ischemia (LAD occlusion) and subsequent reperfusion.
  Groups: Placebo or CDR132L, n=6 per group.
  Treatment: twice, on day 3 and day 28 post-MI, 0.3 mg/kg intracoronary and 0.5 mg/kg intravenously, respectively (FIG. 8).
  Endpoint: 8 weeks post-MI. Primary outcome measures: EF and LV remodeling.
5.3 Results:
  CDR132L treatment averts maladaptive remodeling and improves function, as determined by measurement of end diastolic volume, end systolic volume, ejection fraction and left ventricular function (FIGS. 9A-D).
  CDR132L treatment improves segmental contractility in segments corresponding to surviving/remote myocardium; cardiac MRI at endpoint: n=6/group, red area: p<0.05 (FIG. 9E).
  CDR132L treatment averts maladaptive remodeling and improves LV viability in the apical area as determined by NOGA, electro-anatomical mapping at endpoint: n=6/group, placebo vs CDR132L: p<0.05 (FIG. 10).
  CDR132L normalizes the tissue expression of pathologic heart failure markers in ANP and BNP and provides a shift in myosin heavy change isoforms, i.e. MYH7/6 ratio (FIG. 11).

Figure 12A:
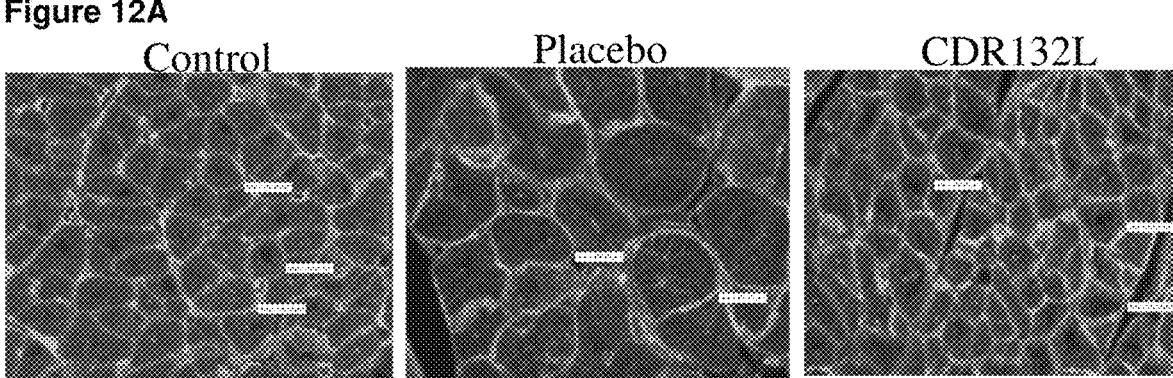
FIG. 12A shows representative photomicrography images of LV area illustrating that at histological level, CDR132L treatment effectively reduces cardiomyocyte hypertrophy in remote LV areas.
Figure 12B:
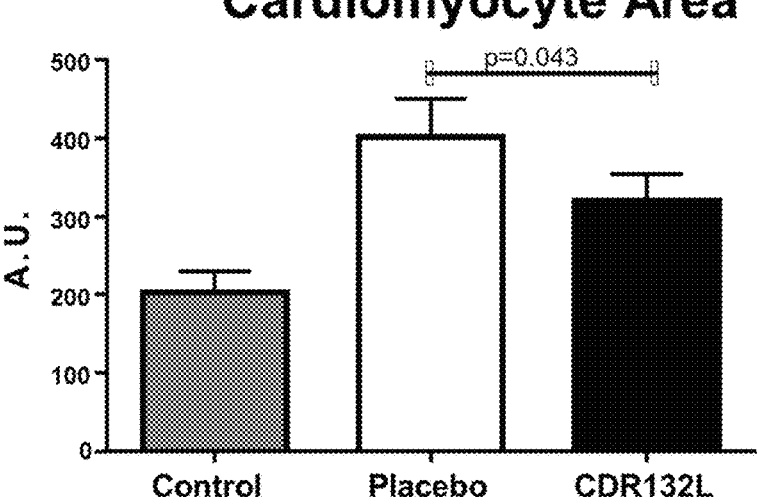
FIG. 12B shows the graphic depiction graphic depiction of cardiomyocyte area.

At histological level, CDR132L treatment effectively reduces cardiomyocyte hypertrophy in remote LV areas representative photomicrography images of LV area (WGA/DAPI Staining 20×) (FIG. 12A) and graphic depiction (FIG. 12B), n=6/group, placebo vs CDR132L: p<0.05.

Figure 13:
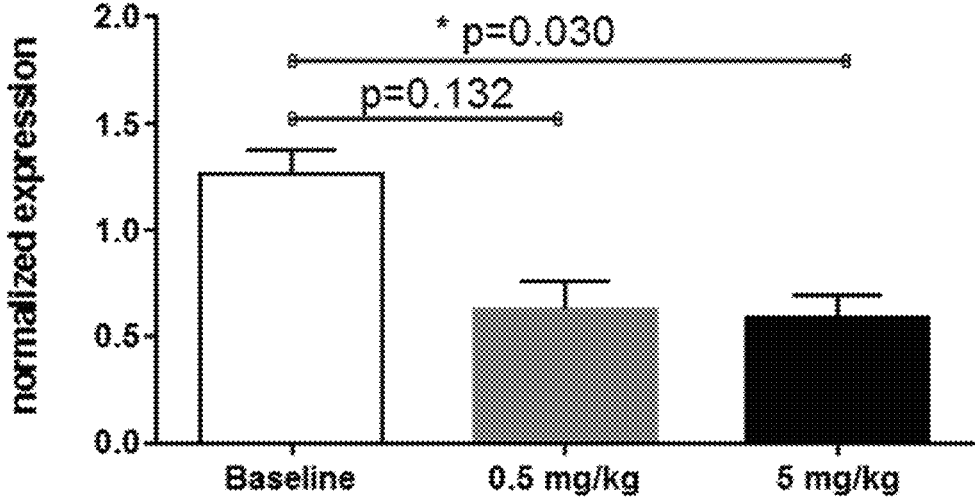
FIG. 13 shows that a single dose of CDR132L treatment dose-dependently silences cardiac miR-132 levels in the pharmacodynamic profile/target engagement of CDR132L in pigs.

Example 6—Pharmacodynamic Profile/Target Engagement of CDR132L in Pigs 6.1 Study Set Up:
  Treatment: 1×, day 0, 0.5 mg/kg or 5 mg/kg intracoronary perfusion, n=3 pigs/group, placebo vs CDR132L: p<0.05.
  qPCR tissue miRNA assay at endpoint (24 h post-treatment).
6.2 Results:
  A single dose of CDR132L treatment dose-dependently silences cardiac miR-132 levels (FIG. 13).

Figure 14:
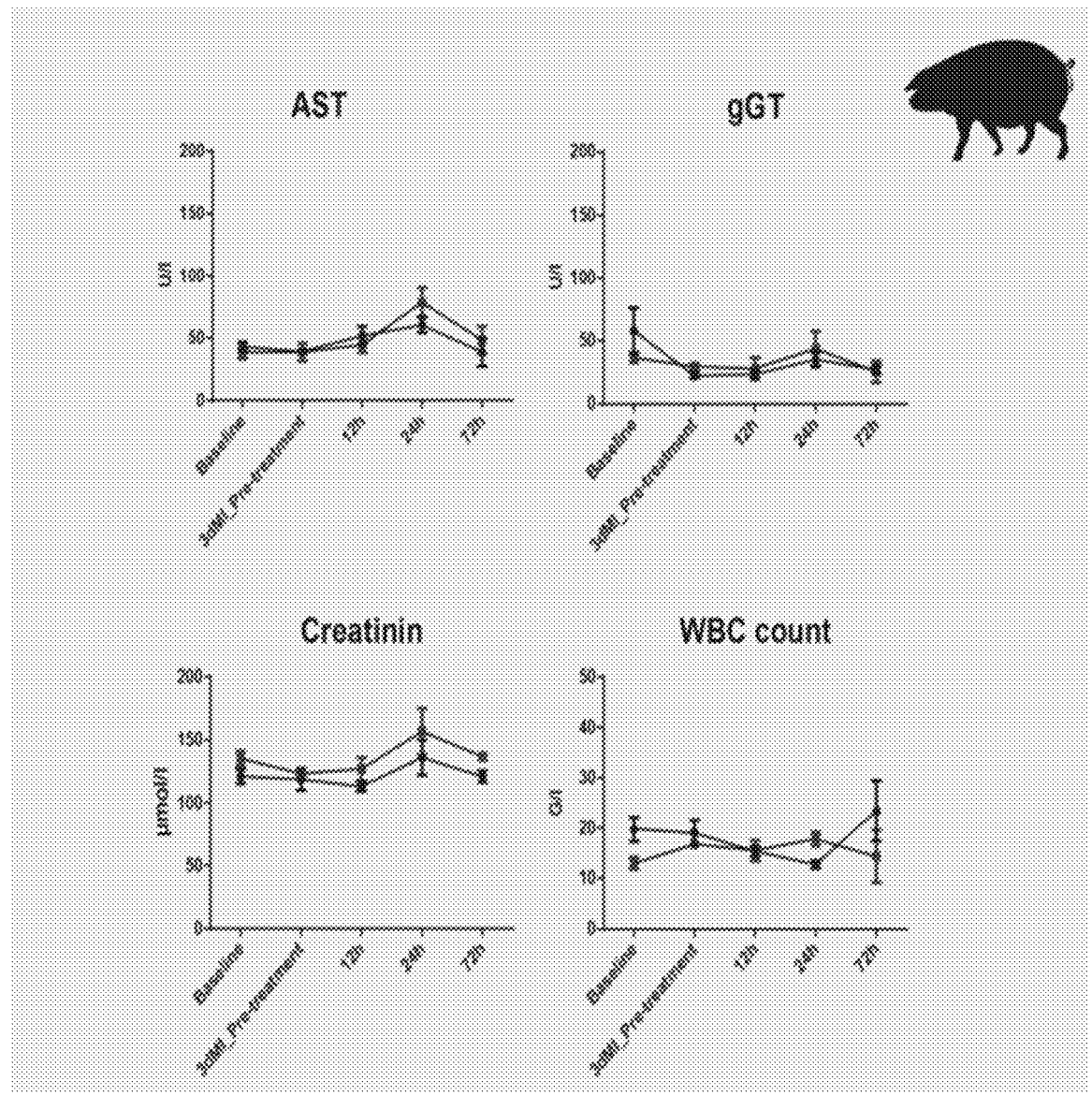
FIG. 14 shows that CDR132L treatment in vivo does not elicit any organ toxicity in pigs.

Example 7—Organ Toxicology Profiling 7.1 Study Set Up:
  Treatment: twice, on day 3 and day 28 post-MI, 0.3 mg/kg intracoronary and 0.5 mg/kg intravenously, respectively.
  Serial blood sampling, endpoint: 72 h-post treatment, n=6 pigs/group, placebo vs CDR132L: p<0.05.
7.2 Results:
  CDR132L treatment in vivo does not elicit any organ toxicity in pigs (FIG. 14).
  Subsequent repeat-dose toxicity studies were carried out in rats and minipigs.
  According to a 4-week toxicity study in rats using intravenous bolus injection of CDR132L at 4, 20 and 100 mg/kg on days 1 and 28, followed by a 4-week recovery period, the "No observed adverse effect level" (NOAEL) in rats was considered to be 20 mg/kg. This corresponds to a human equivalent dose of 3.23 mg/kg body weight.
  According to a 4-week toxicity study in minipigs using intravenous bolus injection of CDR132L at 4, 20 and 40 mg/kg on days 1 and 28, followed by a 4-week recovery period, the "No observed effect level" (NOEL) in minipigs was considered to be 40 mg/kg. This corresponds to a human equivalent dose of 36.36 mg/kg body weight.

Figure 15A:
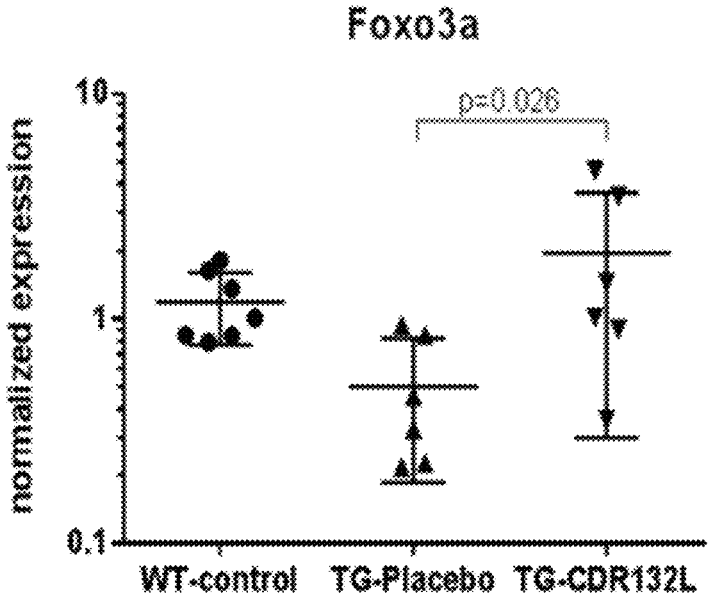
FIGS. 15A and 15B show cardiac FoxO3 and Serca2, respectively, mRNA levels were measured in control and miR-132 TG mice treated with intraperitoneal injection of either control scrambled oligonucleotide or CDR132L, weekly, 4 times.
Figure 15B:
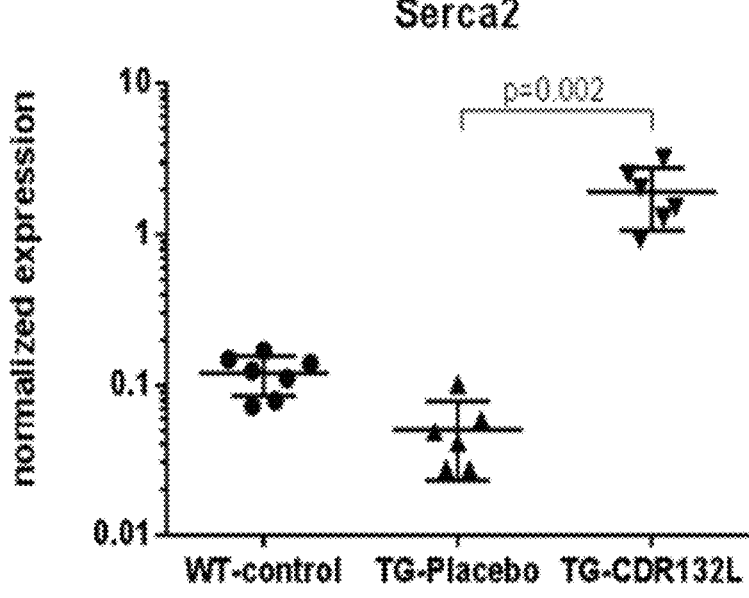

Example 8—Cardiac Levels of FoxO3 and SERCA2 mRNA in a Mouse Model of Heart Failure Cardiac FoxO3 and Serca2 mRNA levels were measured in control and miR-132 TG mice treated with intraperitoneal injection of either control scrambled oligonucleotide or CDR132L, weekly, 4 times. All values represent mean±SEM. * P<0.05 (FIGS. 15A and 15B).

Example 9—Comparison of Different Oligonucleotides

The purpose of this study was to evaluate therapeutic effect of the novel miR-132-3p inhibitor CDR132L according to the prevent invention with two comparative oligonucleotides. The two comparative oligonucleotides exhibit the same oligonucleotide sequence and a phosphorothioate backbone as CDR132L but differ in the distribution of LNA building blocks within the molecule. CDR2u1 harbors two LNA building blocks at the 5' and the 3' end, while for CDR301 each nucleotide carries an LNA building block.

To test the efficiency, the different oligonucleotides were administered to neonatal rat cardiomyocytes (NRCMs). Effects of this treatment were monitored by quantitative real-time PCR (qRT-PCR) following alterations in expression of miR-132-3p and its known target gene FoxO3 (Forkhead box O3).

Figure 16:
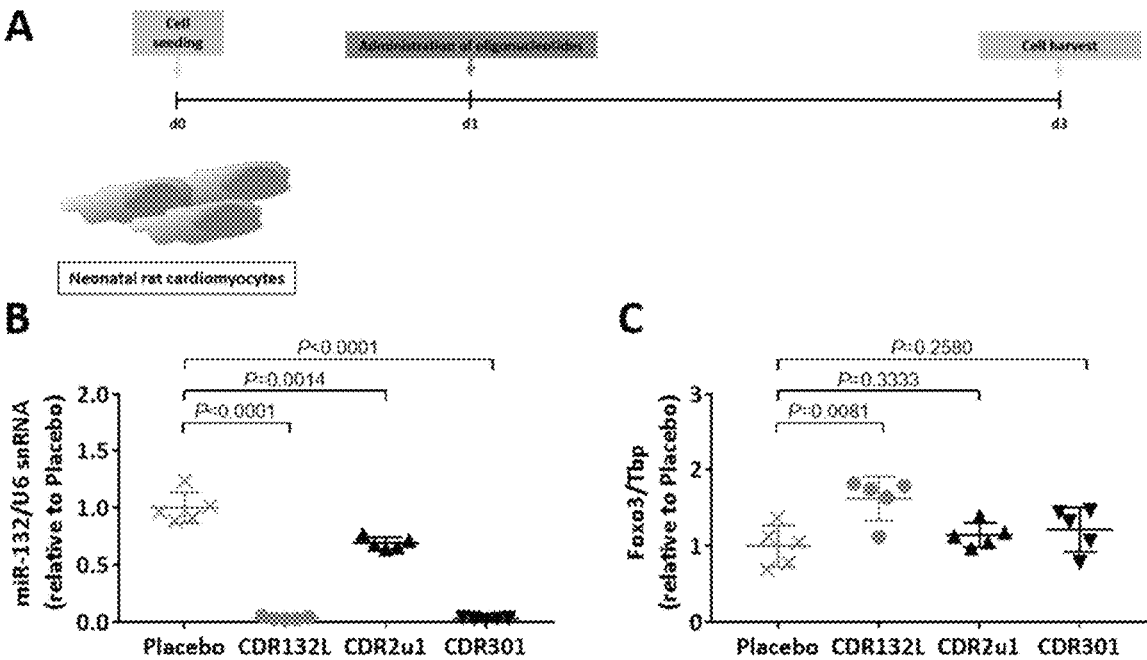
FIG. 16: (A) shows the overview of the experimental set up of the comparison of different oligonucleotides on NRCMs. (B) shows the expression levels of miR-132-3p after treatment with CDR132L, CDR2u1 or CDR301. (C) shows the expression levels of the miR-132-3p target gene Forkhead box O3 (FoxO3) after treatment with CDR132L, CDR2u1 or CDR301.

The experimental design and the results are shown in FIG. 16: (A) Overview of the experimental setup. Neonatal rat cardiomyocytes were seeded on day 0 and treated with the oligonucleotides CDR132L, CDR2u1 or CDR301 (100 nM each) on day 1. At the endpoint, cells are harvested for gene expression analysis. (B) Expression levels of miR-132-3p after treatment with CDR132L, CDR2u1 or CDR301. (C) Expression levels of the miR-132-3p target gene Forkhead box O3 (FoxO3) after treatment with CDR132L, CDR2u1 or CDR301. Data are mean±SD. P values oligonucleotides versus placebo were determined by two-tailed Student's t test.

Treatment of NRCMs with CDR132L and CDR301 led to a significant reduction of miR-132-3p levels by 96%, while CDR2u1 reduced the miRNA expression by 30% (FIG. 16A-B). Further, treatment with CDR132L led to a significant depression of the miR-132-3p target gene Foxo3, which was not achieved with CDR2u1 and CDR301 (FIG. 16C).

In summary, our data demonstrate a superior inhibitory effect of CDR132L compared to CDR2u1 and CDR301 indicated by significantly lowered expression levels or miR-132-3p and significant repression of its target gene FoxO3.

Example 10—Effects of CDR132L in Cardiac Fibrosis

The purpose of this study was to evaluate antifibrotic therapeutic effects of CDR132L in an in vivo model of fibrosis.

Figure 17:
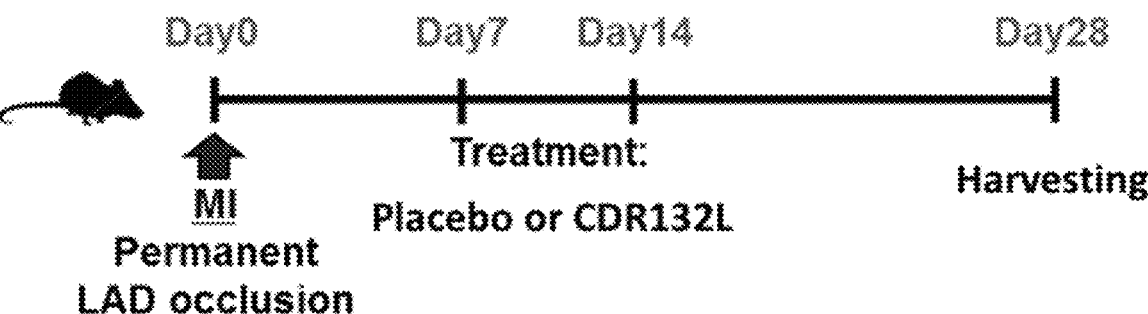
FIG. 17 shows the experimental design of the effects of CDR132L in cardiac fibrosis in an in vivo mouse model.

For in vivo proof of antifibrotic activity, the mouse model of myocardial infarction (MI) by permanent left anterior descending coronary artery (LAD) ligation in C57BL/6N mice was used. CDR132L treatment was applied at day 7 and 14 placebo (scrambled oligo analogue to CDR132L, 20 mg/kg) and CDR132L (20 mg/kg). Groups included the control operated group (sham operated mice) and LAD-ligated mice (MI, myocardial infarction), receiving either placebo or CDR132L: Sham+placebo, Sham+CDR132L, MI+placebo, MI+CDR132L. n=6-7/group. The experimental design is described in FIG. 17. The assessment of the antifibrotic effect of CDR132L in vivo in post MI heart failure is shown in FIG. 18. Fibrosis (shown as % of collagen deposition detected by Picro-sirius red (PSR) staining and Collagen Type III Alpha 1 Chain (Col3a1) gene expression relative to β-Actin) was attenuated after MI by treatment with CDR132L. Groups included the control operation group (sham operated mice) and LAD ligated mice (MI), receiving either placebo (black column) or CDR132L (white column): Sham+placebo, Sham+CDR132L, MI+placebo, MI+CDR132L. Statistical test (unpaired t-test) was done between MI mice treated with placebo or CDR132L. ** p<0.01, n=6-7/group.

Figure 18A:
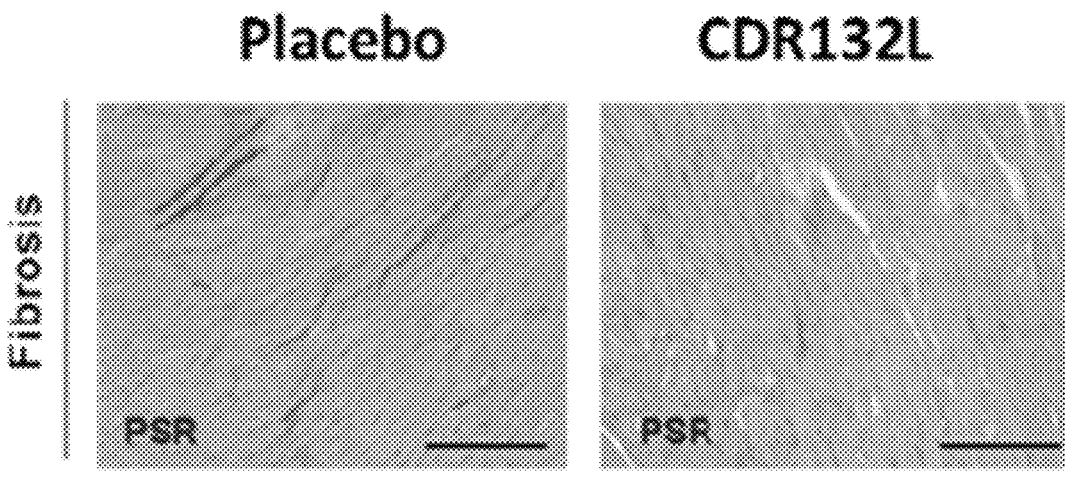
FIG. 18A shows the histological results showing that fibrosis was attenuated after CDR132L treatment.
Figure 18B:
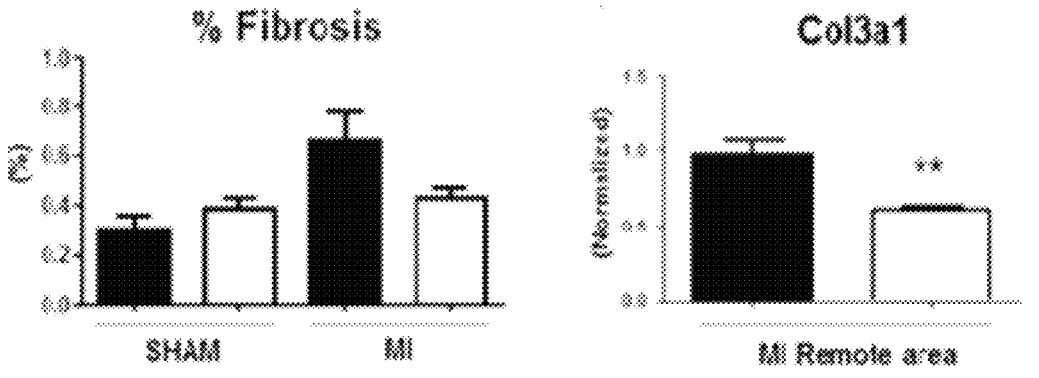
FIG. 18B is the graphic representation showing attenuation of fibrosis at molecular level, with reduced gene expression for fibrosis markers like Collagen Type III Alpha 1 Chain (Col3a1).

According to the histological results, fibrosis was attenuated after CDR132L treatment (FIG. 18A). This was confirmed at molecular level, with reduced gene expression for fibrosis markers like Collagen Type III Alpha 1 Chain (Col3a1) (FIG. 18B).

Example 11—Effects of CDR132L in Pulmonary and Hepatic Fibrosis

The antifibrotic effect of CDR132L was tested in in vitro models for pulmonary and hepatic fibrosis. For that, human primary fibroblasts derived from liver (human primary liver fibroblasts, HPLF, PeloBiotech) and lung (normal human primary lung fibroblasts, NHLF, Lonza) were stimulated with pro-fibrotic agents and treated with CDR132L. Therapeutic effects of CDRL132L were monitored by following key processes within the fibrotic pathway including proliferation rate and alterations in expression of fibrotic marker genes at endpoint. In addition, expression of miR-132-3p was assessed to prove effective CDR132L treatment.

To determine cell proliferation, a Cell Proliferation ELISA (Enzyme-linked Immunosorbent Assay) Kit (provided by Roche) was used. This colorimetric assay allows to quantitate cell proliferation based on the measurement of BrdU (bromodeoxyuridine) incorporated in newly synthesized DNA of proliferating cells. The amount of incorporated BrdU has been detected and quantified. Absorbance values directly correlate to the amount of DNA synthesis and hereby to the number of proliferating cells in the respective microcultures. Gene expression has been assessed using quantitative real-time PCR (qRT-PCR) measuring expression levels of miR-132-3p and fibrotic markers including Collagen 1A1 (COL1A1), Collagen 1A2 (COL1A2), and Matrix Metallopeptidase 2 (MMP2).

Figure 19:
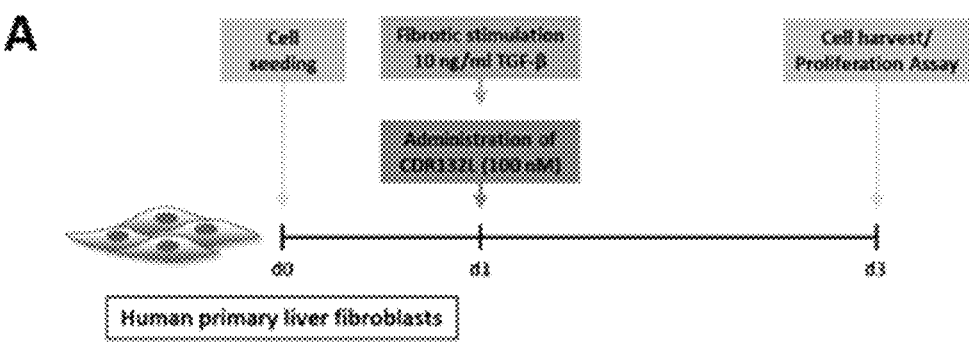
FIG. 19: (A) shows the overview of the experimental setup of the in vitro model of liver fibrosis. (B) shows the expression levels of miR-132-3p after treatment with CDR132L. (C) shows the proliferation assessed by monitoring of BrdU incorporation during DNA synthesis. (D1), (D2), and (D3) show the expression levels of fibrotic marker genes [Collagen 1A1 (COL1A1), Collagen 1A2 (COL1A2), and Matrix Metallopeptidase 2 (MMP2)], respectively.
Figure 19:
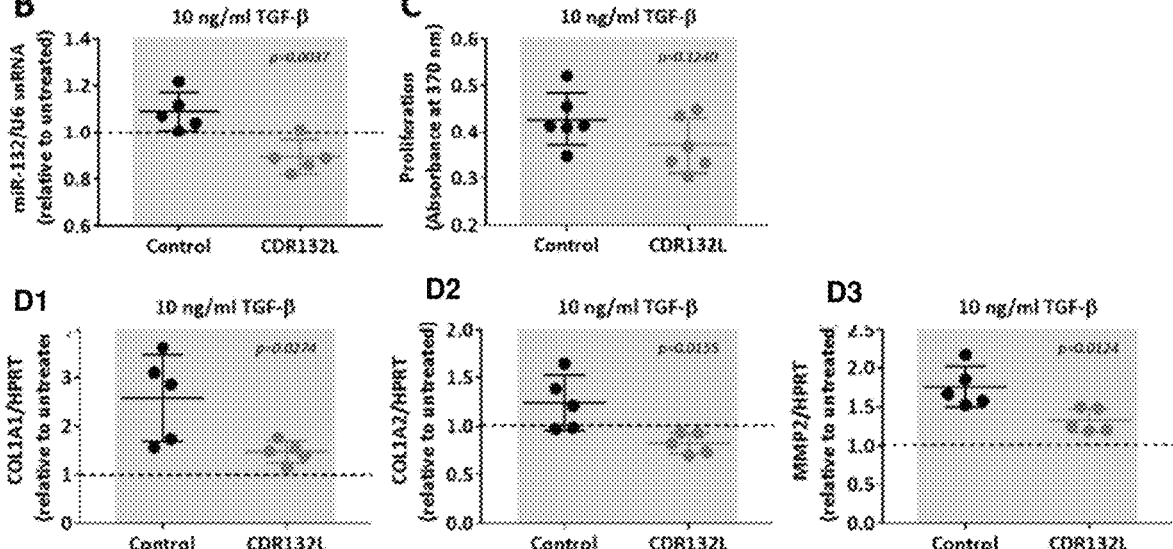

FIG. 19 refers to the in vitro model of liver fibrosis: (A) Overview of the experimental setup. Human primary liver fibroblasts (provided by PeloBiotech) were seeded on day 0 and treated with fibrotic stimulus (10 ng/ml TGF-β in normal growth medium (complete fibroblast medium supplemented with 10% FBS)) and CDR132L (100 nM) on day 1. At endpoint, cell proliferation and gene expression of fibrotic markers have been assessed. (B) Expression levels of miR-132-3p after treatment with CDR132L. (C) Proliferation assessed by monitoring of BrdU incorporation during DNA synthesis. The BrdU reagent has been added to the medium 20 h before endpoint. (D1-D3) Expression levels of fibrotic marker genes (Collagen 1A1 (COL1A1), Collagen 1A2 (COL1A2), and Matrix Metallopeptidase 2 (MMP2)). In (B) and (D) dashed line indicates expression level of unstimulated control cells. Data are mean±SD. P values CDR132L versus control were determined by two-tailed Student's t test.

Stimulation of HPLFs with transforming growth factor beta (TGF-β) (FIG. 19A) led to slight induction of miR-132-3p that was significantly reduced by CDR132L treatment (FIG. 19B). Further, this compound reduced fibroblast proliferation (FIG. 19C) and fibrotic gene expression including COL1A1, COL1A2, and MMP2 (FIGS. 19D1-19D3).

Figure 20:
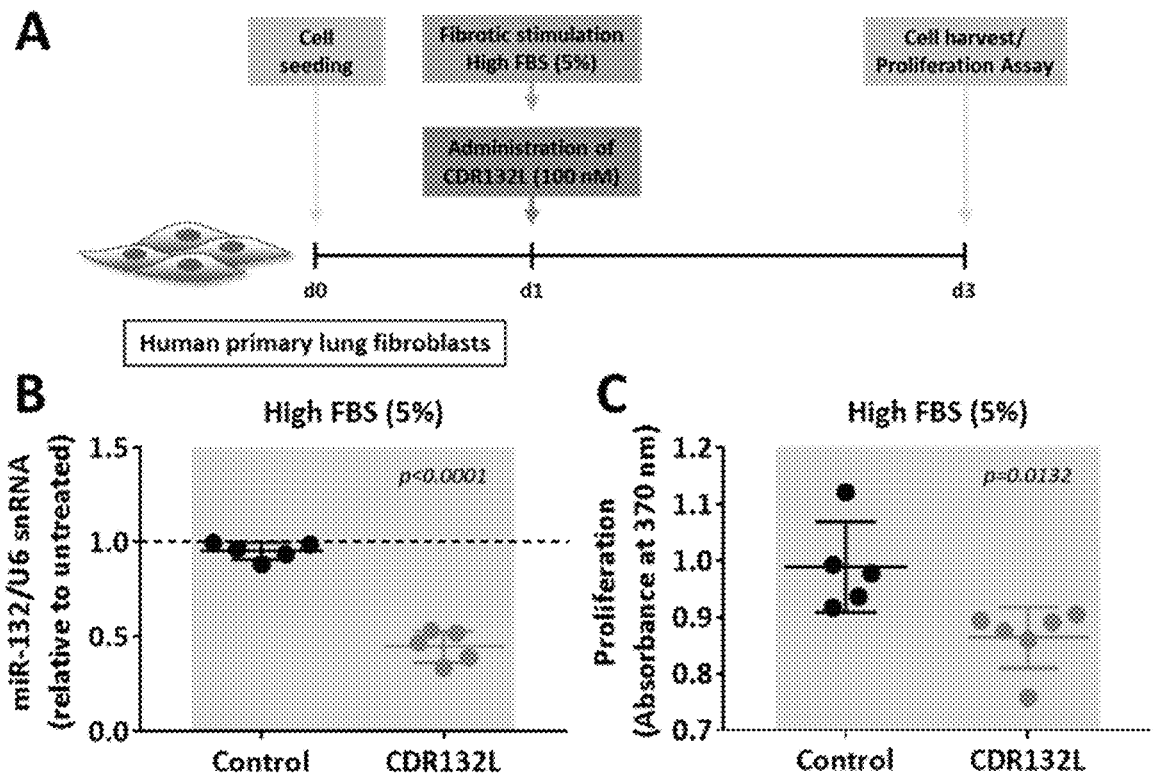
FIG. 20: (A) illustrates the overview of the experimental setup of the in vitro model of lung fibrosis in human primary lung fibroblasts. (B) shows the expression levels of miR-132-3p after treatment with CDR132L. (C) shows the proliferation assessed by monitoring of BrdU incorporation during DNA synthesis.

FIG. 20 refers to the in vitro model of lung fibrosis: (A) Overview of the experimental setup. Normal human lung fibroblasts (provided by Lonza) were seeded on day 0 and treated with fibrotic stimulus (High FBS (5%) in fibroblast growth medium and CDR132L (100 nM) on day 1. At endpoint, cell proliferation and gene expression have been assessed. (B) Expression levels of miR-132-3p after treatment with CDR132L. (C) Proliferation assessed by monitoring of BrdU incorporation during DNA synthesis. The BrdU reagent has been added to the medium 20 h before endpoint. In (B) dashed line indicates expression level of unstimulated control cells. Data are mean±SD. P values CDR132L versus control were determined by two-tailed Student's t test.

In NHLF cells, after fibrotic stimulation with high FBS (5% compared to normal growth conditions of 2% FBS) (FIG. 20A) no elevation of miR-132-3p was observed (FIG. 20B). Nevertheless, treatment with CDR132L led to a significant reduction of the targeted microRNA (FIG. 20B) and fibroblast proliferation (FIG. 20C).

In summary, our data demonstrate a significant anti-fibrotic effect of the oligonucleotide analogue CDR132L in liver- or lung-derived fibroblasts as well as in cardiac tissue. We assume this effect may be based on the drug's anti-proliferative capacity, and/or on its effect on the extracellular matrix protein expression.

Example 12—Protocol and Results of a Human Clinical Study 12.1 Protocol:
Rationale Current state-of-the-art heart failure pharmacotherapy is mainly limited to less advanced disease stages (New York Heart Association stage I and II; NYHA I/II). The drugs however cannot prevent progression to advanced stages (NYHA III and IV), which are associated with frequent hospitalizations and a 1-year mortality that exceeds 70% (13). As a last resort, implanted pumps (left ventricular assisting devices, LVAD) and ultimately heart transplantation may be the only life-saving options for a very few end-stage heart failure patients.

Thus, novel, efficient, disease-halting therapeutics, that reduce mortality and hospitalization are urgently needed to offer curative hope for patients. The present inventors' approach offers a new opportunity to revolutionize medical practice, improve patient care and reduce costs of heart failure care.

The mode of action of CDR132L has the following key elements forming the basis of its role as a next generation drug in heart failure:

a) normalization of aberrant cardiac miR-132 levels,
b) normalization of calcium signaling and contractility, and cardiac function,
c) improvement in cardiac autophagy and homeostasis, and
d) attenuation of maladaptive cardiac remodeling.

Results of preclinical studies demonstrated that the safety profile of CDR132L is adequate to progress with clinical development.

Therefore, this study plans to evaluate the safety, pharmacokinetics and some pharmacodynamic parameters in patients with stable heart failure of ischemic origin (NYHA I-III) based on the significant therapeutic effects demonstrated in the clinically relevant large animal study. For this study it is planned to apply a dose escalation scheme.
Primary Objective To assess the safety of one single and one repeated dose of CDR132L in patients with stable heart failure of ischemic origin (NYHA stages I, II and III).
Secondary Objective To characterize the pharmacokinetic (PK) profile of CDR132L in patients with stable heart failure of ischemic origin.
Exploratory Objective To determine the effect of CDR132L on pharmacodynamic (PD) parameters.
Primary Endpoints The primary endpoint is the safety of CDR132L as measured by:

The incidence and severity of treatment-emergent adverse events (TEAEs),
Proportion of subjects with clinically significant changes in laboratory safety tests (hematology, chemistry, coagulation and urinalysis),
Proportion of subjects with morphological and/or rhythm abnormalities on electrocardiogram (ECG),
Proportion of subjects with clinically significant changes in ECG time intervals (PR, QRS, QT and QTc intervals),
Proportion of subjects with clinically significant changes in vital signs (systolic blood pressure, diastolic blood pressure and pulse rate),
Proportion of subjects with clinically significant changes in organ damage markers of cardiac (high-sensitivity cardiac troponin T), renal (creatinine), and hepatic (aspartate transaminase and alanine transaminase) damage and of decongestion (N-terminal pro b-type natriuretic peptide).
Secondary Endpoints PK parameters derived by non-compartmental methods including maximum observed plasma concentration ($C_{max}$), time to maximum plasma concentration ($t_{max}$), area under the plasma concentration-time curve from time zero to last detectable plasma concentration ($AUC_{0-t}$), area under the plasma concentration-time curve from time zero extrapolated to infinity ($AUC_{0-inf}$), blood clearance (CL), terminal elimination rate constant ($\lambda z$), terminal elimination half-life ($t_{1/2}$), volume of distribution (Vdss).
Exploratory Endpoints The PD parameters including but not limited to the following biomarkers: microRNA 132 (miR-132) for target engagement, N-terminal pro b-type natriuretic peptide (NT-pro-BNP) for decongestion and Neutrophil gelatinase-associated lipocalin (NGAL) as marker for cardiac remodeling. Additional parameters may be required.

To identify biomarkers which may (1) predict response to treatment with CDR132L, (2) explain variability in drug PK/PD, (3) predict susceptibility to drug-drug interactions or (4) predict the occurrence of safety issues. The aim of such exploratory research will be to develop a better understanding of intrinsic and extrinsic factors that may affect the pharmacokinetics of CDR132L in human subjects. This will not include any genome (DNA) sequencing of patients.
Study Design This is a Phase I, randomized, double-blind, placebo-controlled study to assess safety, pharmacokinetics and pharmacodynamic parameters of CDR132L in patients with stable heart failure of ischemic origin (NYHA stages I-III).

A maximum of twenty-eight patients will be enrolled. The four planned cohorts with maximum cohort size are listed below. Each of these cohorts will consist of up to 7 patients. Patients will be randomized to receive intravenous 15 min infusion of either CDR132L or placebo in a ratio of up to 5:2.

Treatment 1 (n=up to 7)-0.32 mg/kg CDR132L; placebo
Treatment 2 (n=up to 7)-1.00 mg/kg CDR132L; placebo
Treatment 3 (n=up to 7)-3.00 mg/kg CDR132L; placebo
Treatment 4 (n=up to 7)-10.00 mg/kg CDR132L; placebo.
Patients will be screened within 41 days prior to entering the study on Day-1. Each subject will receive verbal and written information followed by signing of the Informed Consent Form (ICF) prior to any screening procedures taking place. Subjects will be admitted to the study unit on Day-1 and will be discharged on Day 4, re-admitted on Day 27 and discharged on Day 31. On Day 1 volunteers will receive either CDR132L or placebo; they will receive a second matching dose when they re-admit on Day 27 with second dosing occurring on Day 28. All patients should be receiving Standard of Care (SoC) therapy for heart failure of ischemic origin, according to the latest European guidelines (14). CDR132L or placebo will be given as add-on therapy to SoC treatment.

All subjects will attend the unit for planned outpatient visits on Days 10-14, 56, 84 and 112. All the assessments performed during the study are detailed in the study schedule of assessments (Table 2 and Table 3). Study design features may be adapted according to the Adaptive Features (Table 4). This study will use a sentinel dosing strategy, for full details see Section 3.3.5.

Number of Subjects

Twenty-eight patients with stable heart failure of ischemic origin were recruited to dosing cohorts 1, 2, 3 and 4.

Main Criteria for Admission

C18036_CDR132L-FIH01_Clinical Study Protocol_v1.0_17Apr.2019 Clinical Study Protocol Template (Version 6) 14 Mar. 2019 Page 16 of 85 Subjects will be included if they are aged between 30 and 80 years with a body mass index (BMI) between 18.0-28.0 kg/m$^2$ and confirmed stable heart failure of ischemic origin.

Main exclusion criteria are: Heart failure of non-ischemic origin (hypertensive heart disease, myocarditis, alcoholic cardiomyopathy and cardiac dysfunction due to rapid atrial fibrillation), current or recurrent disease; not including stable heart failure (e.g. hematological, neurological, endocrine, immunological, renal, hepatic or gastrointestinal or other conditions) that could affect the action, absorption, or disposition of CDR132L, or could affect clinical assessments or clinical laboratory evaluations.

Test Treatment(s) and Mode of Administration

Cohort 1:0.32 mg/kg CDR132L intravenous infusion (15 min; 20 ml) on Days 1 and 28 (n=5)

Cohort 2:1.00 mg/kg CDR132L intravenous infusion (15 min; 20 ml) on Days 1 and 28 (n=5)

Cohort 3:3.00 mg/kg CDR132L intravenous infusion (15 min; 20 ml) on Days 1 and 28 (n=5)

Cohort 4:10.00 mg/kg CDR132L intravenous infusion (15 min; 20 ml) on Days 1 and 28 (n=5)

Reference Treatment(s) and Mode of Administration

Intravenous infusion (15 min; 20 ml) of placebo (n=8) to match CDR132L.

Criteria for Evaluation

—Safety Analysis

Safety assessments will include standard laboratory safety tests (hematology, coagulation, biochemistry and urinalysis), vital signs (systolic blood pressure [SBP], diastolic blood pressure [DBP], respiratory rate, pulse rate and tympanic temperature), physical examinations, 12-lead ECG (RR, PR, QRS, QT, QTcF intervals and heart rate [HR]), telemetry, biomarkers assessment and adverse event monitoring.

—Pharmacokinetic Analysis

The following pharmacokinetic parameters will be calculated from measured plasma concentrations of CDR132L: maximum observed plasma concentration ($C_{max}$), time to maximum plasma concentration ($t_{max}$), area under the plasma concentration-time curve from time zero to last detectable plasma concentration ($AUC_{0-t}$), area under the plasma concentration-time curve from time zero extrapolated to infinity ($AUC_{0-inf}$), blood clearance (CL), terminal elimination rate constant ($\lambda z$), terminal elimination half-life ($t_{1/2}$), volume of distribution (Vdss).

—Pharmacodynamics Analysis

Pharmacodynamic assessments will be exploratory and will be evaluated by taking blood samples to determine the concentration of the following biomarkers: microRNA 132 (miR-132) for target engagement, N-terminal pro b-type natriuretic peptide (NT-pro-BNP) for decongestion and Neutrophil gelatinase-associated lipocalin (NGAL) as marker for cardiac remodelling. Additional parameters may be required.

Statistical Methods

A statistical analysis plan (SAP) containing detailed statistical methodology will be written and signed off before the database hard lock. The plan may be updated to reflect adaptive features of the study as appropriate.

—Statistical Analysis of Safety Parameters

Adverse events (AE), vital signs, ECG parameters and clinical laboratory data will be listed and summarised using descriptive statistics.

The number (and %) of subjects who had any AEs will be summarized for each dose. All AEs will be listed by system organ class (SOC) and preferred term (PT) assigned to the event using Medical Dictionary for Regulatory Activities (MedDRA). Furthermore, these events will be summarized by the maximum intensity. The number of subjects who had drug-related AEs will also be summarized. Any serious adverse events (SAEs) and/or adverse events that led to withdrawal will be listed.

—Statistical Analyses of Pharmacokinetic Parameters

Plasma concentrations will be listed and summarized by time point. The PK parameters will be listed for each subject and summarized for each treatment group using descriptive statistics. To preliminarily assess dose proportionality for $C_{max}$ and AUC, dose-normalized plasma $C_{max}$, $AUC_{0-t}$ and $AUC_{0-inf}$ will be calculated and summarized descriptively. In addition, a power model with log (PK parameter) as response variable and log(dose) as predictor will be fitted to the data for plasma $C_{max}$, $AUC_{0-t}$ and $AUC_{0-inf}$. A slope of 1 in this model corresponds to dose proportionality. The slope will be estimated with its 2-sided 90% and 95% Cl.

—Statistical Analyses of Pharmacodynamic Parameters

The PD parameters data will be listed and summarized: absolute values along with changes from baseline, using descriptive statistics.

For each dose group, the relationship between plasma concentration and PD parameters will be investigated using graphical representation of each PD parameter against plasma concentrations. This relationship will be investigated using the intersection of the PK and relevant PD population. Where the summary statistics and graphical representations indicate a relationship between plasma concentration and PD parameter, an appropriate statistical model may be developed to further explain this relationship.

12.2 Patient Characteristics:

28 Patients with stable heart failure (HF) of ischemic origin (NYHA 1-3) were included in a randomized double-blind, placebo-controlled study. Patient characteristics further included type 2 diabetes, previous myocardial infarction events, atrial fibrillation, arterial hypertension, percutaneous intervention and/or coronary artery bypass surgery. Left ventricular ejection fraction was in the range between 31% and 56%.

Patients received background treatment for co-morbidities at the physician's discretion and were on stable therapy for their individual HF condition. Most patients received dual/triple therapy (a beta blocker combined with either an ACE inhibitor or an angiotensin-receptor blocker and a mineralocorticoid antagonist). 2 Placebo and 2 Verum patients had a biventricular pacemaker; 3 Verum patients had an implanted cardioverter defibrillator (ICD).

12.3 Preliminary Results:

Pharmacokinetic (PK) Profile

The CDR132L PK profile in human confirmed safety profile with no signs for accumulation. The PK profile and translatability from pig to human were confirmed. High level of dose linearity in $C_{max}$ and AUC allowed projection of PK parameters for other doses (e.g. 5 mg/kg). Based on the preliminary results of the phase Ib study, the starting dose for a clinical study phase II is suggested between 3 and 10 mg/kg followed by maintenance dose between about of 3 and 5 mg/kg.

Target Engagement

Circulating miR-132 levels in the verum patients were significantly and dose-dependently decreased and remained low over time (until the study endpoint at day 112).

ECG Results

Most Verum patients had an abnormal ECG at screening. Many of them showed normalization or substantial dose-dependent improvement (e.g. normalization of T waves; QRS narrowing or absence of left bundle branch block (LBBB) and/or right bundle branch block (RBBB); normalization of R progression) under CDR132L treatment. None had worsening ECGs from baseline under CDR132L treatment. Based on the QT and QTc data no hint for a proar-rhythmic potential was found.

Pharmacodynamic (PD) Parameters

A positive impact on ejection fraction (EF) was found in most of the treated patients. NT-proBNP as cardiac safety marker was not adversely affected by CDR132L treatment. Patients at the highest dose group (10 mg/kg) showed a robust decrease in NT-proBNP levels at day 28 and 122 in comparison to baseline. 2× treatment with CDR132L (dose 1-10 mg/kg) led to an improvement of EF and/or reduction of NT-proBNP values in >50% of all patients. A reduction in Isovolumic Relaxation Time (IVRT), an important marker of left ventricular relaxation, was found in patients with EF>45%, suggesting a benefit in patients with diastolic dysfunction.

Biomarkers

Cardiac fibrosis biomarkers procollagen type I C-terminal propeptide (PICP) and Galectin-3 (Gal-3) show reduced levels in CDR132L-treated HF patients indicating anti-fibrotic effects. Further, fibrosis biomarker Matrix Metallo-proteinase 1 (MMP-1) was positively correlated with circulating levels of miR-132 and reduced in patients of higher dose groups (cohorts 3 and 4). At the study endpoint, MMP-1 levels were below limit of detection in cohort 4.

Safety and Tolerance

No serious adverse events (SAE) were found. No patho-logic effects or safety signals were identified in biochemical and hematological parameters, vital signs, and ECG:

12.4 Conclusion:

CDR132L was well tolerated by human heart failure patients and did not show any signs of toxicity in doses up to 10 mg/kg.

Example 13—CDR132L Therapy Monitoring by Quantification of Circulating miR-132-3p in Plasma The purpose of this study was to assess levels of miR-132-3p in plasma as a biomarker for CDR132L therapy monitoring.

Figure 21:
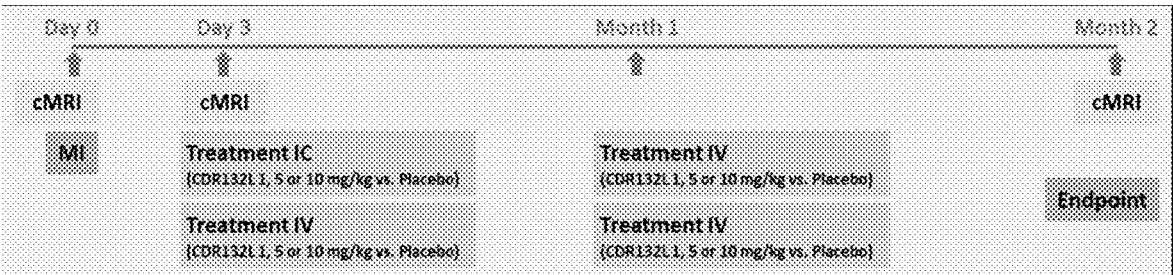
FIG. 21 illustrates the placebo-controlled porcine model of myocardial infarction (MI) induced heart failure (HF).

Circulating miR-132-3p was measured in plasma samples from a placebo-controlled porcine model of myocardial infarction (MI) induced heart failure (HF) (FIG. 21). Ani-mals underwent MI and were subjected to different treat-ment schemes of CDR132L including two applications of on day 3 and month 1 (intracoronary/intravenous (ICIV) versus intravenous/intravenous (IVIV)) and three dose levels of CDR132L (low: 1 mg/kg, mid: 5 mg/kg, or high: 10 mg/kg).

The study was accompanied by serial blood sampling until the month 2. In plasma samples from the endpoint, circulating levels of miR-132-3p were monitored by quan-titative real-time PCR (qRT-PCR) using TaqMan probes for miR-132-3p. Data were normalized to a synthetic microRNA (cel-miR-39) spike-in added during the RNA extraction procedure.

Figure 22:
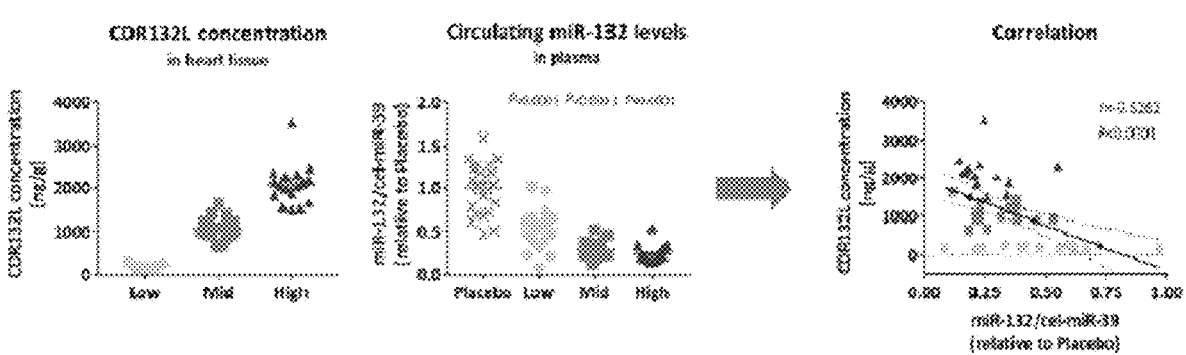
FIG. 22 shows a correlation analysis of CDR132L concentration in heart tissue (LV MI remote region) of all included animals (IVIV and ICIV) and circulating levels of miR-132-3p normalized to cel-miR-39.

Treatment with CDR132L led to a dose-dependent increase of the drug substance in the target organ, the heart, and significant reduction of functional miR-132-3p in plasma samples. FIG. 22 shows a correlation analysis of CDR132L concentration in heart tissue (LV MI remote region) of all included animals (IVIV and ICIV) and circu-lating levels of miR-132-3p normalized to cel-miR-39. Data are individual animals as means±SEM. P values were assessed by non-parametric two-tailed Mann-Whitney U Test (left panel). Correlation was performed by Pearson product-moment correlation and Spearman rank-order cor-relation (right panel). Accordingly, circulating miR-132-3p strongly correlated with the concentration of CDR132L in cardiac tissue of treated animals. These data indicate that circulating miR-132-3p is an indicative marker for the presence of CDR132L in heart tissue.

Figure 23:
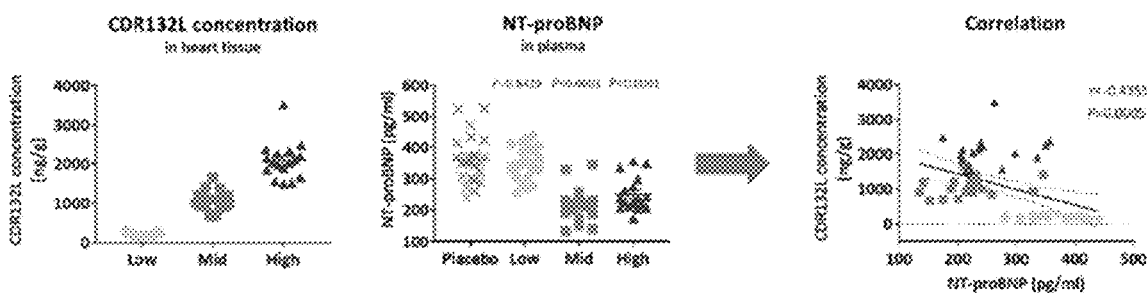
FIG. 23 shows a correlation analysis of CDR132L concentration in heart tissue (LV MI remote region) of all included animals (IVIV and ICIV) and plasma levels of NT-proBNP (N-terminal pro b-type natriuretic peptide).

We further assessed, if other established biomarkers indi-cate presence of CDR132L in cardiac tissue. N-terminal pro b-type natriuretic peptide (NT-proBNP) is well known as a marker of cardiac stress, which correlates with heart failure severity. In line with miR-132-3p levels, FIG. 23 shows a correlation analysis of CDR132L con-centration in heart tissue (LV MI remote region) of all included animals (IVIV and ICIV) and plasma levels of NT-proBNP (N-terminal pro b-type natriuretic peptide). Data are individual animals as means±SEM. P values were assessed by non-parametric two-tailed Mann-Whitney U Test (left panel). Correlation was performed by Pearson product-moment correlation and Spearman rank-order cor-relation (right panel). A reduction of NT-proBNP was observed in plasma of CDR132L treated animals (FIG. 23). Nevertheless, dose-dependency was less evident and the correlation to cardiac CDR132L less significant.

Aside the relation between circulating miR-132 in plasma and CDR132L in heart, we evaluated if the drug substance efficiently inhibits its target microRNA miR-132-3p. Func-tional miR-132-3p levels were significantly reduced in car-diac tissue (LV MI remote region) and this reduction was stronger the higher the dose.

Figure 24:
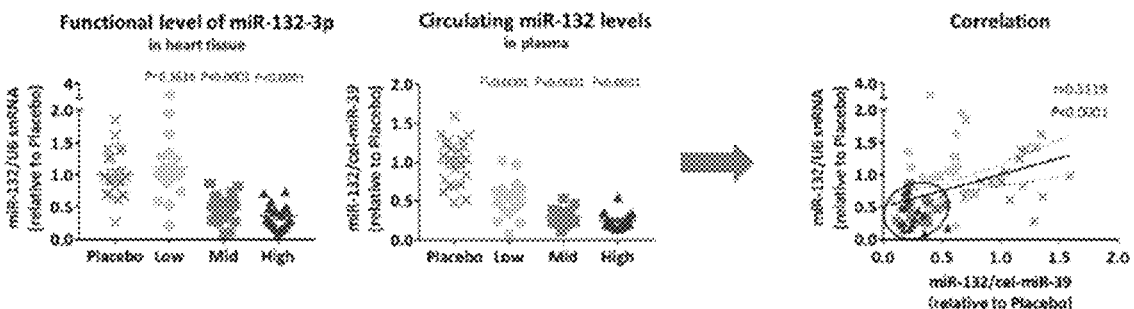
FIG. 24 shows a correlation analysis of functional miR-132-3p levels in heart tissue (LV MI remote region) of all included animals (IVIV and ICIV) and circulating levels of this microRNA normalized to cel-miR-39.

FIG. 24 shows a correlation analysis of functional miR-132-3p levels in heart tissue (LV MI remote region) of all included animals (IVIV and ICIV) and circulating levels of this microRNA normalized to cel-miR-39. Data are indi-vidual animals as means±SEM. P values were assessed by non-parametric two-tailed Mann-Whitney U Test (left panel). Correlation was performed by Pearson product-moment correlation and Spearman rank-order correlation (right panel). Correlation of plasma and cardiac miR-132-3p unrevealed a significant negative association between both parameters, indicating that plasma levels of miR-132-3p level are indicative for the activity of CDR132L on its target miR-132-3p.

It has been shown that CDR132L treatment ameliorates cardiac function after MI. Accordingly, we tested whether this functional improvement, the change in left ventricular ejection fraction (EF) compared between day 3 post MI and month 2 (delta EF), corresponds with circulating miR-132-3p. A significant negative correlation was observed for both parameters, indicating that circulating miR-132-3p level are indicative for the improvement of cardiac function.

Figure 25:
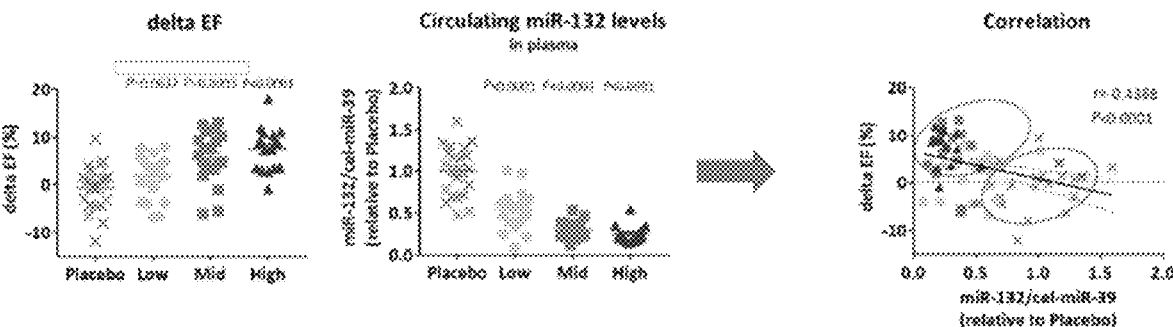
FIG. 25 shows a correlation analysis of delta EF (improvement of EF from day 3 to month 2) of all included animals (IVIV and ICIV) and circulating levels of this microRNA normalized to cel-miR-39.

FIG. 25 shows a correlation analysis of delta EF (improvement of EF from day 3 to month 2) of all included animals (IVIV and ICIV) and circulating levels of this microRNA normalized to cel-miR-39. Data are individual animals as means±SEM. P values were assessed by non-parametric two-tailed Mann-Whitney U Test (left panel). Correlation was performed by Pearson product-moment correlation and Spearman rank-order correlation (right panel).

The negative association was as strong as the correlation between the functional improvement and the cardiac stress marker NT-proBNP.

Figure 26:
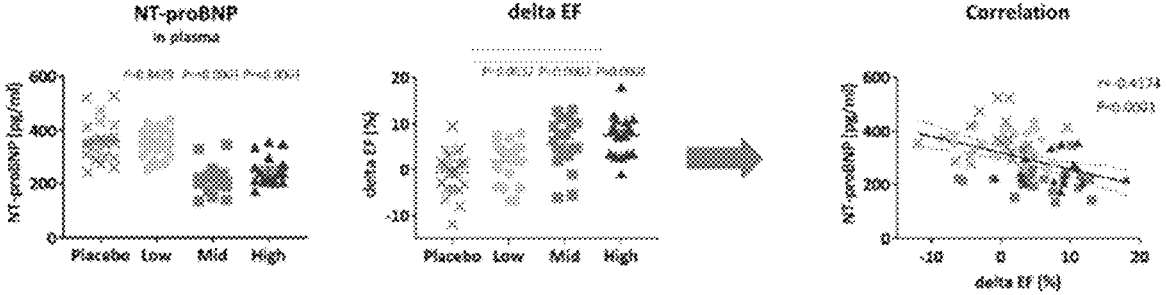
FIG. 26 shows a correlation analysis of plasma levels of NT-proBNP of all included animals (IVIV and ICIV) and delta EF (improvement of EF from day 3 to Month 2).

FIG. 26 shows a correlation analysis of plasma levels of NT-proBNP of all included animals (IVIV and ICIV) and delta EF (improvement of EF from day 3 to Month 2). Data are individual animals as means±SEM. P values were assessed by non-parametric two-tailed Mann-Whitney U Test (left panel). Correlation was performed by Pearson product-moment correlation and Spearman rank-order correlation (right panel).

In addition, a low level of circulating NT-proBNP corresponds with a low level of circulating miR-132-3p in a linear manner.

Figure 27:
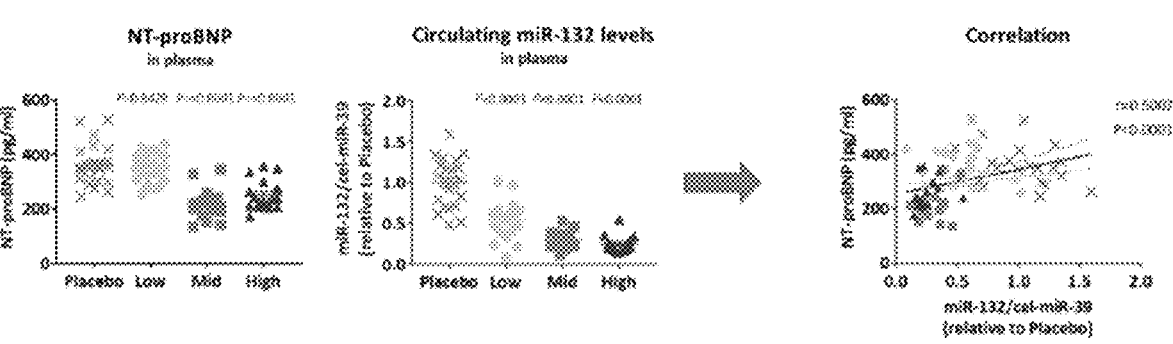
FIG. 27 shows a correlation analysis of plasma levels of NT-proBNP of all included animals (IVIV and ICIV) and circulating levels of miR-132-3p normalized to cel-miR-39.

FIG. 27 shows a correlation analysis of plasma levels of NT-proBNP of all included animals (IVIV and ICIV) and circulating levels of miR-132-3p normalized to cel-miR-39. Data are individual animals as means±SEM. P values were assessed by non-parametric two-tailed Mann-Whitney U Test (left panel). Correlation was performed by Pearson product-moment correlation and Spearman rank-order correlation (right panel).

Example 14—CDR132L in Subacute Heart Failure 14.1 Study Aim: Test Efficacy of CDR132L in a Pig Model of Post MI-Subacute Heart Failure (HF)

14.2 Study Outline:

Model of HF following myocardial infarction with 56 day follow-up in 135 animals Domestic pigs with slow weight gain ("mangalica breed")

Figure 28:
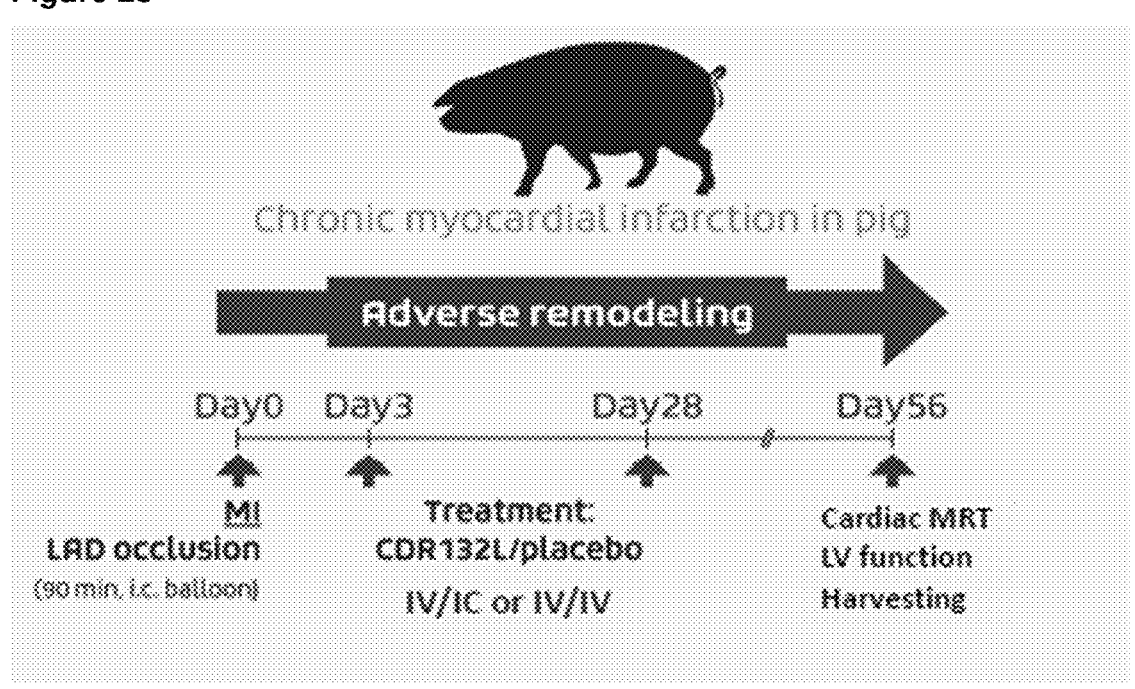
FIG. 28 illustrates the study outline for adverse remodeling of chronic myocardial infarction in pig post MI-subacute heart failure (HF).

Placebo control and 3 dose groups 1, 5, 10 mg/kg b.w. treated twice, at days 3 & 28 (FIG. 28).

Comparison of intracoronary/intravenous (IC/IV) and intravenous/intravenous (IV/IV) applications.

Animals considered for data analysis: 79 animals.

14.3 Results:

Change in Ejection Fraction Delta EF (EF Day 56-EF Day 3)

NB: Inclusion criteria, EF on Day 3<40%

Figures 29, 30:
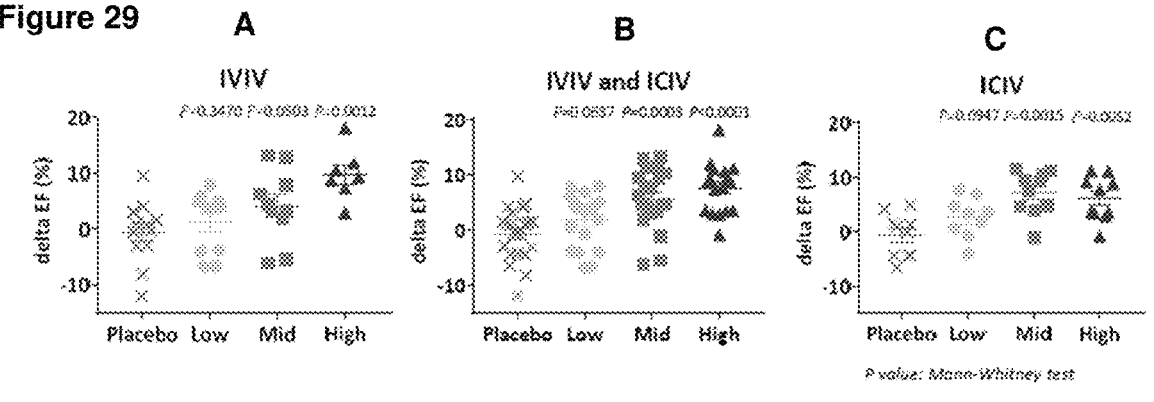
FIG. 29 shows changes in EF from day 3 to day 56 (delta EF) post MI were found in the mid- and high-dose IV/IV and IC/IV groups.
FIG. 30 shows changes in Fibrosis development were found in the mid and high dose group.

Significant changes in EF from day 3 to day 56 (delta EF) post MI were found in the mid- and high-dose IV/IV and IC/IV groups indicating functional improvement (FIG. 29).

Correlation of Circulating NT-proBNP and Delta EF (Day 56-Day 3)

Post-MI HF-related increase of NT-proBNP was reversed in the mid and high dose groups at day 56. A low level of circulating NT-proBNP concentration corresponds with an improvement of cardiac function indicated by increased delta EF. NT-proBNP serves as a potential biomarker for indication of target engagement (c.f. Example 13).

Fibrosis (%) at Endpoint (Day 56) in LV MI Remote Region

NB: Inclusion criteria, EF on Day 3<40%

Significant changes in Fibrosis development were found in the mid and high dose group contributing to functional improvement (FIG. 30).

Therapeutic response (day 56)

NB: Inclusion criteria, EF on Day 3<40%

Figure 31:
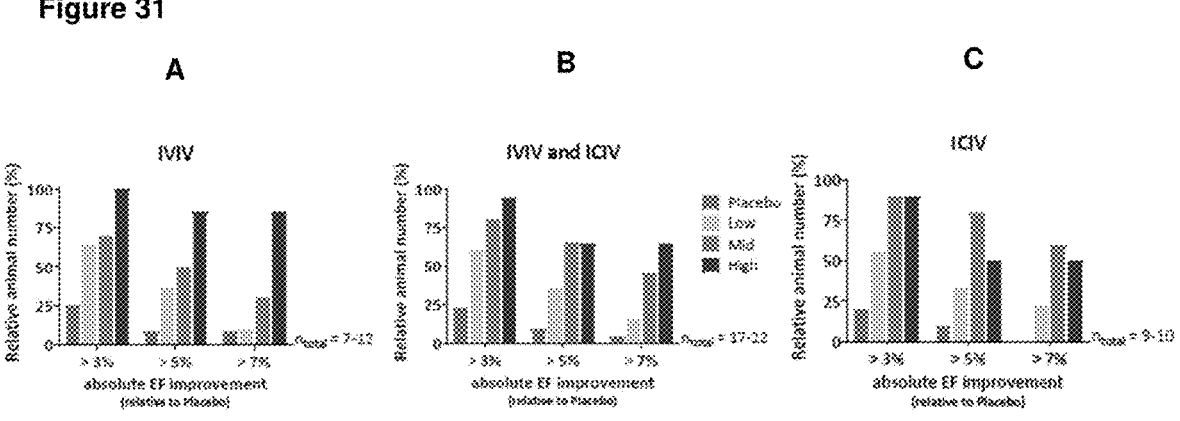
FIG. 31 shows a responder analysis illustrating a dose-dependent response in EF improvement in IVIV and ICIV.

A responder analysis unraveled a dose-dependent response in EF improvement. 85.7% of the IVIV high dose group showed a delta EF of >7% whereas only 4.6% of all placebo animals showed recovery of >7% (FIG. 31).

14.4 Conclusions:

CDR132L effectively improves cardiac function, based on gold-standard cardiac MRI measurements in a clinically relevant and accepted large animal model of post-MI HF. A linear dose relationship for improvement in cardiac function was observed. IVIV high dose group showed a 10.38% increase in EF at day 56 when compared to day 3 (placebo-corrected). The demonstrated efficacy of CDR132L is of high clinical relevance (for comparison cardiac cell transplantation increases at best 3-4% EF).

Example 15—CDR132L for the Treatment of Chronic Heart Failure 15.1 Study Aim: Test Efficacy of CDR132L in a Pig Model of Post MI-Chronic Heart Failure (HF)

Figure 32:
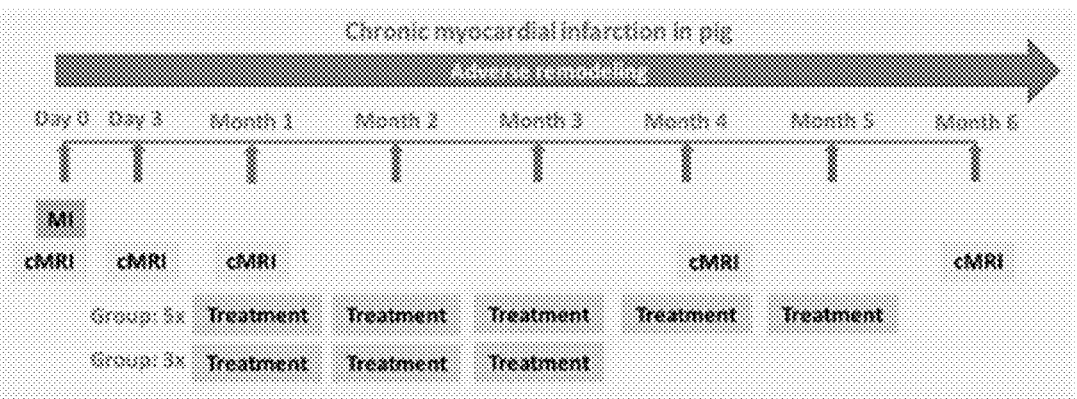
FIG. 32 illustrates the study outline for adverse remodeling of chronic myocardial infarction in pig post MI-subacute heart failure (HF) with 6 months follow up.

15.2 Study Outline:

Validation of CDR132L efficacy in a chronic post-MI heart failure (HF) pig model Chronic model of post-MI HF with 6 months follow up (FIG. 32)

Domestic pigs with slow weight gain ("mangalica breed")

Three treatment arms:

5× monthly Placebo

5× monthly CDR132L

3× monthly CDR132L

Dose: 5 mg/kg

Route of administration: IV

Animals considered for data analysis: 29 animals.

15.3. Results:

Ejection fraction (EF)

NB: Inclusion criteria, EF on month 1<40%

Figure 33:
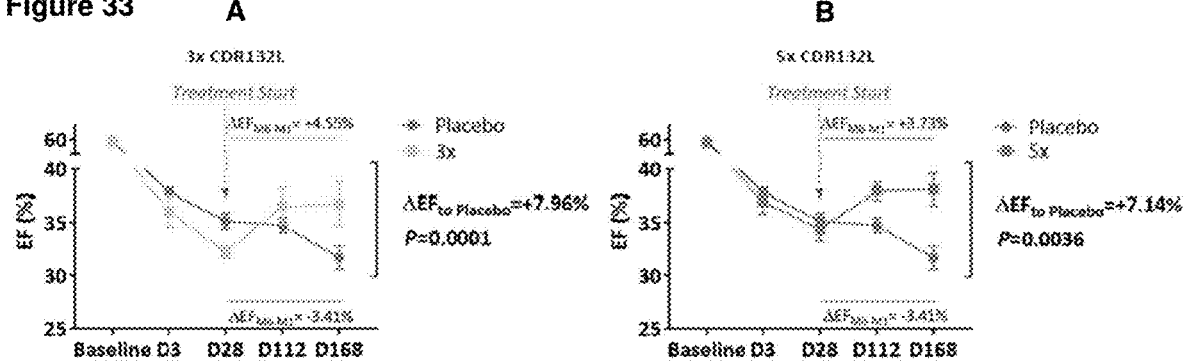
FIG. 33 shows a strong correlation between the treatment quantity and EF improvement (delta EF M6-M1).

Significant >7% EF changes from month 1 to month 6 post MI were found in all treatment groups compared to placebo (FIG. 33).

Responder Analysis

NB: Inclusion criteria, EF on month 1<40%

A strong correlation between the treatment quantity and EF improvement (delta EF M6-M1) was observed (FIG. 33). 87.5% of the 5× treatment group showed a delta EF of >7% whereas only 2 out of 11 placebo animals showed recovery of >3%.

Levels of CDR132L and miR-132-3p after 6 Months

NB: Inclusion criteria, EF on Day Month 1<40%

Figure 34:
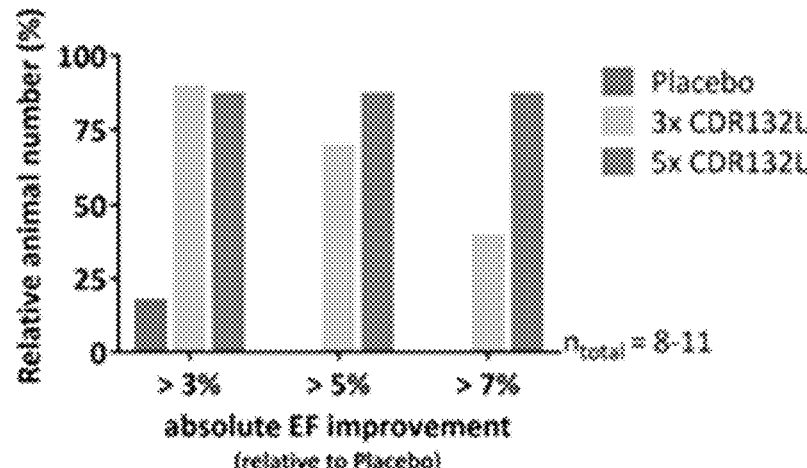
FIG. 34 shows a dose dependent CDR132L heart tissue distribution (LV MI remote region).
Figure 35:
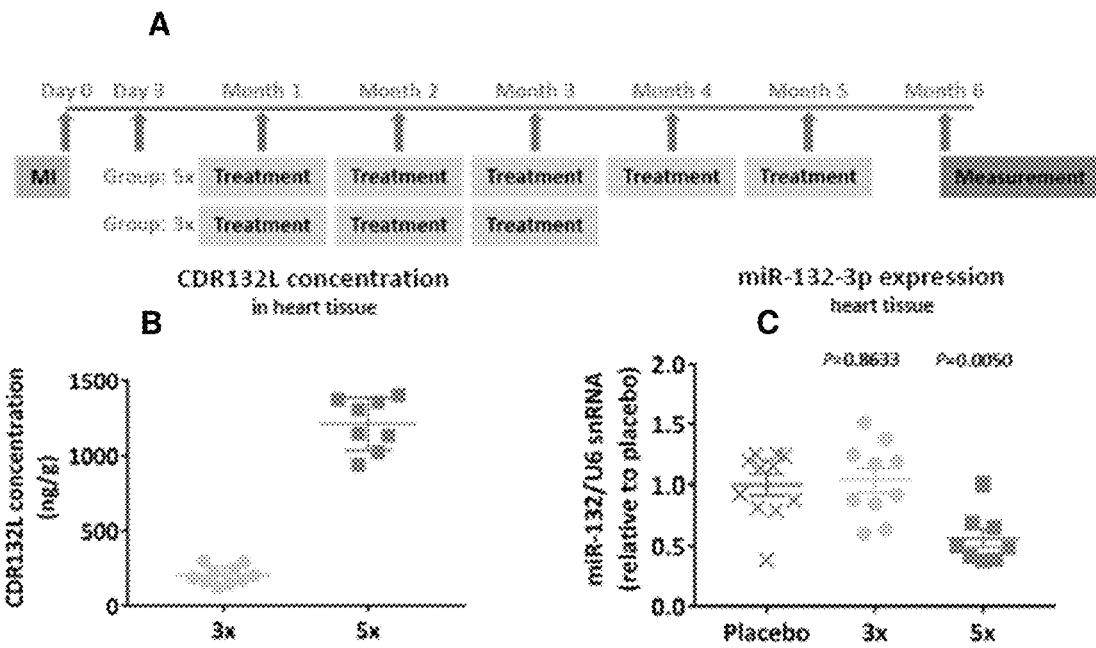
FIG. 35: (A) illustrates the study outline post MI with 6 months follow up. (B) shows a correlation analysis of CDR132L concentration in heart tissue. (C) shows a correlation analysis of functional miR-132-3p levels in heart tissue.

A dose dependent CDR132L heart tissue distribution (LV MI remote region) was observed. The CDR132L tissue concentration corresponds with a low functional level of miR-132-3p (FIG. 34).

Left ventricle end systolic volume (LVESV)

CDR132L treatment showed a beneficial effect on adverse left ventricular remodeling and significantly attenuated the post-MI enlargement of LVESV over a 6 month follow-up period in both treatment groups compared to placebo.

Left Atrium (LA)

Post-MI chronic atrial remodeling was reduced by CDR132L treatment as assessed by imaging. LA volume and LA index (LA volume normalized to body surface area) were significantly reduced in both treatment groups compared to placebo.

Systolic Function and Contractility

Systolic function and contractility were significantly improved by CDR132L treatment in the post-MI failing heart, assessed by invasive hemodynamic measurement at the 6-month endpoint. Analysis of load-independent parameters revealed a CDR132L treatment-dependent improvement of myocardial contractility (end-systolic pressure-volume relationship and preload recruitable stroke work) which clearly translated into better overall systolic function.

Diastolic Function

CDR132L treatment significantly improved diastolic function. The global diastolic parameter (minimum rate of pressure change in the ventricle) and the load-independent parameter EDPVR (end-diastolic pressure volume relationship), a sensitive marker of cardiac stiffness and capacitance, were both improved by CDR321L treatment.

15.4 Conclusions:

CDR132L strongly improves cardiac function in a pig model of chronic heart failure. A 7.14% increase in EF was demonstrated at month 6 in animals receiving five monthly treatments with CDR132L (placebo-corrected). 87.5% of animals responded to treatment by over 7% improvement in EF. No therapy-related adverse events or changes in hematology or laboratory chemistry were observed. The demonstrated efficacy of CDR132L is clinically highly relevant as a treatment option in chronic heart failure.

Further, CDR132L treatments given monthly, effectively improve remodeling, systolic function (e.g. cardiac contractility) and diastolic function (e.g. cardiac relaxation) in a chronic post-MI heart failure model.

Example 16—Pharmacokinetic Study

Figure 36:
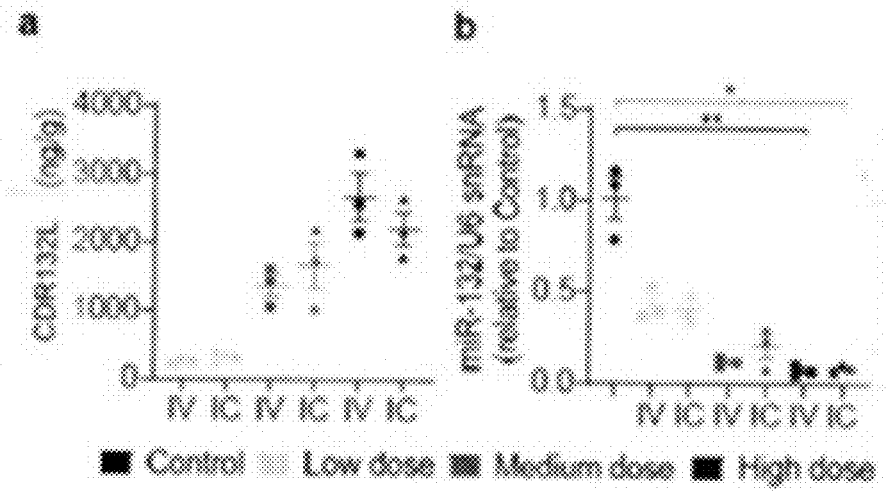
FIG. 36 shows the pharmacokinetic assessment of CDR132L. (a) and (b) show dose-dependent tissue exposure in the cardiac tissue samples comparable both for intravenous (IV) and intracoronary (IC) perfusion administration of CDR132L. (c1) and (c2) show a strong inverse correlation between cardiac antimiR-132 concentration and functional miR-132 levels independent of the route of administration. (d) shows the half-life of the compound in cardiac tissue. (e) shows the plasma a bi-phasic elimination of the compound with a rapid alpha phase and a long beta phase.
Figure 36:
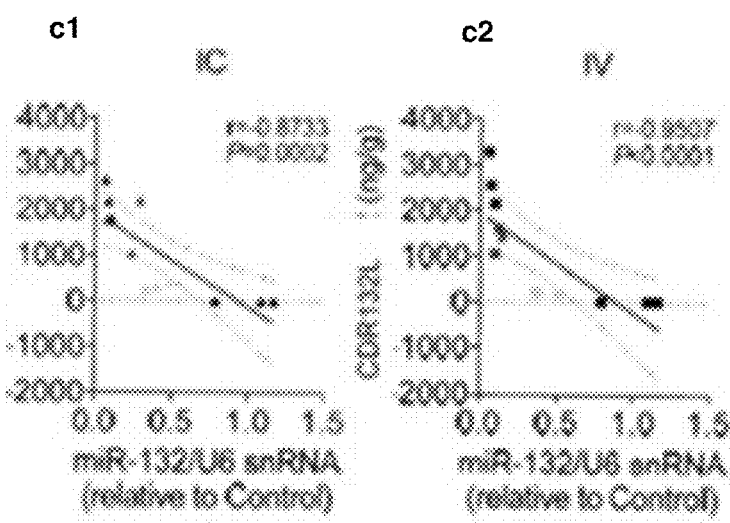
Figure 36:
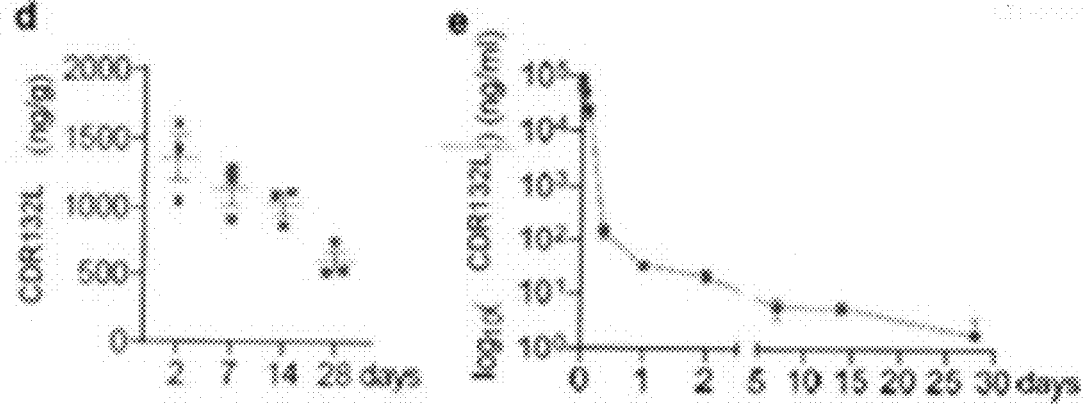

To further assess the therapeutic potential of CDR132L, we designed a large animal pharmacokinetic (PK) study to assess tissue exposure and distribution in the target tissue of our compound in pigs. Intravenous (IV) administration is a clinically preferred application route, however many novel therapy approaches rely on alternative route of administrations, such as intracoronary (IC) perfusion, as often in the case for cardiac gene therapy studies. We found dose-dependent tissue exposure in the cardiac tissue samples comparable both for IV and IC administration of CDR132L (FIG. 36 a,b). CDR132L activity was confirmed by the reciprocal dose dependent reduction of the target miR-132 level compared to untreated control animals. there was a strong inverse correlation between cardiac antimiR-132 concentration and functional miR-132 levels (FIG. 36 c) independent of the route of administration. The half-life of the compound in the cardiac tissue was calculated to be approx. 3 weeks (FIG. 36 d) and for plasma a bi-phasic elimination of the compound with a rapid alpha phase and a long beta phase was found (FIG. 36 e).

REFERENCES

1. Barry, S. P.; Townsend, P. A. (2010). What causes a broken heart-Molecular insights into heart failure. Int Rev Cell Mol Biol 284, 113-179.
2. Datta, S. R.; Brunet, A.; Greenberg, M. E. (1999). Cellular survival: a play in three Akts. Genes Dev. 13, 2905-2927.
3. DeBosch, B. J.; Muslin, A. J. (2008). Insulin signaling pathways and cardiac growth. J Mol Cell Cardiol. 44, 855-864.
4. Frescas, D.; Valenti, L.; Accili, D. (2005). Nuclear trapping of the forkhead transcription factor FoxO1 via Sirt1-dependent deacetylation promotes expression of glucogenetic genes. J Biol Chem. 280, 20589-20595.
5. Glas, D. J. (2010). PI3 kinase regulation of skeletal muscle hypertrophy and atrophy. Curr Top Microbiol Immunol. 346, 267-278.
6. Gottlieb, R. A.; Gustafsson, A. B. (2011). Mitochondrial turnover in the heart. Biochim Biophys Acta. 1813, 1295-1301.
7. Kolk, M. V.; Meyberg, D.; Dense T.; Tang-Quam, K. R.; Robbins R. C.; Reichenspurner, H.; Schrepfer. S (2009), J. Vis Exp. 32, pii: 1438. doi: 103791/1438
8. McMullen, J. R.; Shioi, T.; Huang, W. Y.; Zhang, L.; Tarnavski, O.; Bisping, E.; Schinke, M.; Kong, S.; Sherwood, M. C.; Brown, J. et al. (2004). The insulin-like growth factor 1 receptor induces physiological heart growth via the phosphoinositide 3-kinase (p110alpha) pathway. J Biol Chem. 279, 4782-4793.
9. Ni, Y. G.; Berenji, K.; Wang, N.; Oh, M.; Sachan, N.; Dey, A.; Cheng, J.; Lu, G.; Morris, D. J.; Castrillon, D. H. et al. (2006). Foxo transcription factors blunt cardiac hypertrophy by inhibiting calcineurin signaling. Circulation. 114, 1159-1168.
10. Ronnebaum, S. M.; Patterson, C. (2010). The foxO family in cardiac function and dysfunction. Annu Rev Physiol. 72, 81-94.
11. Skurk, C.; Izumiya, Y.; Maatz, H.; Razeghi, P.; Shiojima, I.; Sandri, M.; Sato, K.; Zeng, L.; Schiekofer, S.; Pimentel, D. et al. (2005). The FOXOSa transcription factor regulates cardiac myocyte size downstream of AKT signaling. J Biol Chem. 280, 20814-23.
12. Ucar, A. et al. (2012), Nat. Commun. 3:1078. doi: 10.1038/ncomms2009.
13. Grech, E. D. & Ramsdale, D. R. (2003), BMJ 326:1259-61.
14. Ponikoskwi, P. et al. (2016), Eur. Heart J. 37:2129-2200.

The invention claimed is:

1. A method for preventing or treating a cardiac disorder in a human subject comprising administering to a human subject in need thereof an effective amount of an oligonucleotide comprising the sequence of formula III:

5'-dA*+T*dG*+G*dC*+T*dG*+T*dA*+G*dA*dC*dT*dG*+T*+
T-3' wherein dA is 2'deoxyadenosine, dG is 2'deoxyguanosine, dC is 2'deoxycytidine and T is thymidine,
wherein +T is an LNA-T building block and +G is an LNA-G building block and wherein
* is a phosphorothioate linkage,
wherein the cardiac disorder is selected from (i) acute or subacute heart failure, (ii) chronic and/or worsening chronic heart failure, (iii) stable heart failure, (iv) a less advanced state of heart failure or from an advanced state of heart failure, (v) heart failure of NYHA stage I and/or II, NYHA stage I, II and/or Ill or of NYHA stage Ill and/or IV, and (vi) right-sided heart failure.

2. The method of claim 1, wherein the oligonucleotide is administered as such or wherein the oligonucleotide is administered conjugated to a heterologous moiety.

3. The method of claim 1, wherein the oligonucleotide is administered in combination with (i) at least one diuretic, (ii) at least one angiotensin-converting enzyme inhibitor, (iii) at least one β-blocker, or (iv) an angiotensin-II-receptor blocker or (v) an If-channel inhibitor or ivabradine or (vi) an angiotensin-receptor-neprilysin-inhibitor, or (vii) an glucose Co-transporter 2 inhibitor, empagliflozinU, and or dapagliflozin, or (viii) stem cell therapeutics, or (ix) anti-miRNAs targeting different pathways, and/or (x) a SGLT-2 inhibitor.

4. The method of claim 1, wherein the human subject suffers from acute or subacute heart failure.

5. The method of claim 1, wherein the human subject suffers from chronic and/or worsening chronic heart failure.

6. The method of claim 1, wherein the human subject suffers from stable heart failure of non-ischemic and/or ischemic origin.

7. The method of claim 1, wherein the human subject suffers from a less advanced state of heart failure or from an advanced state of heart failure.

8. The method of claim 1, wherein the human subject suffer from heart failure and has an implanted pump or a left ventricular assisting device.

9. The method of claim 1, wherein the human subject suffer from left-sided heart failure, systolic heart failure, or diastolic heart failure or a condition associated with systolic heart failure and/or diastolic heart failure.

10. The method of claim 1, wherein the human subject suffers from right-sided heart failure.

11. The method of claim 1, wherein the oligonucleotide is administered to a human subject in a dose of about 0.1-100 mg/kg body weight per application, or in an amount of about 3-10 mg/kg body weight per application.

12. The method of claim 1, wherein the oligonucleotide is administered parenterally, by injection or infusion, or by intravenous or subcutaneous injection.

13. The method of claim 1, wherein the oligonucleotide is administered topically.

14. A method of monitoring therapy with an oligonucleotide as defined in claim 1, comprising determining the amount and/or activity of miR-132 in a sample from a subject to whom the oligonucleotide has been administered, wherein the determination is carried out once or several times during the course of therapy.

15. The method of claim 14, wherein the amount of miR-132 in a sample from a circulating body fluid selected from blood, plasma, serum or fractions thereof, is quantitatively determined.

16. The method of claim 14, wherein based on the result of the determination, at least one of the following steps is carried out:

(i) determining whether the subject to be treated is a responder to the therapy, (ii) adjusting the dose of the oligonucleotide to be administered, and (iii) adjusting a time interval of the oligonucleotide to be administered.

17. The method of claim 1, wherein the oligonucleotide is administered to the human subject in a regimen, selected from:

daily administration, administration each second day, administration each third day, and administration each fourth day, wherein the oligonucleotide is administered parenterally, particularly by intravenous or subcutaneous injection.

18. The method of claim 17, wherein the oligonucleotide is administered in a body weight dependent dose.

19. The method of claim 18, wherein the oligonucleotide is administered in a dose of 0.01 mg/kg body weight to 50 mg/kg body weight, in a dose of 0.02 mg/kg body weight to 10 mg/kg body weight, or in a dose of 0.05 mg/kg body weight to 5 mg/kg body weight per administration.

20. The method of claim 17, wherein the oligonucleotide is administered in a fixed dose.

21. The method of claim 20, wherein the oligonucleotide is administered in a fixed dose of 1 mg to 5000 mg, in a fixed dose of 2 mg to 1000 mg, or in a fixed dose of 5 mg to 500 mg per application.

22. The method of claim 1, wherein the oligonucleotide is administered to a human subject in a regimen, selected from:

weekly administration, administration each second week, administration each third week, administration each fourth week or each month, administration each sixth week, administration each second month administration each third month, administration each sixth month, and administration once per year, wherein the oligonucleotide is administered parenterally, particularly by intravenous or subcutaneous injection.

23. The method of claim 22, wherein the oligonucleotide is administered in a body weight dependent dose.

24. The method of claim 23, wherein the oligonucleotide is administered in a dose of 0.01 mg/kg body weight to 50 mg/kg body weight, in a dose of 0.05 mg/kg body weight to 20 mg/kg body weight, in a dose of 0.1 mg/kg body weight to 10 mg/kg body weight or in a dose of 3 mg/kg body weight to 10 mg/kg body weight per application.

25. The method of claim 22, wherein the oligonucleotide is administered in a fixed dose.

26. The method of claim 25, wherein the oligonucleotide is administered in a fixed dose of 1 mg to 5000 mg, in a fixed dose of 5 mg to 2000 mg, or in a fixed dose of 10 mg to 1000 mg per application.

27. The method of claim 26, wherein the oligonucleotide is administered in a starting dose of 1 or 2 starting doses, and subsequently in at least one maintenance dose, which is different from the starting dose.

28. The method of claim 1, wherein the oligonucleotide is administered by a demand-based regimen, particularly comprising the steps:

(i) measuring the amount of miR132 in a body fluid sample, e.g. in a whole blood, serum or plasma sample or urine, of a subject being treated with the oligonucleotide, and (ii) administering the oligonucleotide in a dose and/or time interval between individual doses as determined according to the measured amount of miR132 in step (i), particularly wherein a new dose of the oligonucleotide is administered if the amount of miR132 in the body fluid sample is found to be above a predetermined value.

29. The method of claim 28, further comprising determining the amount and/or activity of a marker, particularly a cardiac and/or a fibrotic marker, before, during and/or after administration of the oligonucleotide.

30. The method of claim 29, wherein the marker is selected from BNP, NT-proBNP, ANP, myosin heavy change isoforms, the MYH7/6 ratio, FoxO3 SERCA2, a collagen deposition and/or fibrotic marker, collagen 1A1, collagen 1A2, collagen 3A1, procollagen type I C-terminal propeptide (PICP), and/or Galectin-3 (Gal-3), and/or a matrix metalloproteinase, Matrix Metalloproteinase 1 (MMP-1) and/or Matrix Metalloproteinase 2 (MMP-2).

31. The method of claim 30, wherein the marker is selected from NT-proBNP, procollagen type I C-terminal propeptide (PICP), and/or Galectin-3 (Gal-3), and/or Matrix Metalloproteinase 1 (MMP-1).

32. The method of claim 31, further comprising determining an ECG parameter during the course of therapy wherein the parameter is selected from measurement of QRS, T waves, left bundle branch block (LBBB) and/or right bundle branch block (RBBB); and/or R progression, before, during and/or after administration of the oligonucleotide.

\* \* \* \* \*

SEQUENCE LISTING

```
<160> NUMBER OF SEQ ID NOS: 3

<210> SEQ ID NO 1
<211> LENGTH: 16
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)..(16)
<223> OTHER INFORMATION: at least one G or T is a bridged nucleotide
```

-continued building block

<400> SEQUENCE: 1
atggctgtag actgtt                                                    16

<210> SEQ ID NO 2
<211> LENGTH: 16
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)..(2)
<223> OTHER INFORMATION: bridged or morpholino nucleotide building block
<220> FEATURE:
<221> NAME/KEY: misc_feature
<222> LOCATION: (4)..(4)
<223> OTHER INFORMATION: bridged or morpholino nucleotide building block
<220> FEATURE:
<221> NAME/KEY: misc_feature
<222> LOCATION: (6)..(6)
<223> OTHER INFORMATION: bridged or morpholino nucleotide building block
<220> FEATURE:
<221> NAME/KEY: misc_feature
<222> LOCATION: (8)..(8)
<223> OTHER INFORMATION: bridged or morpholino nucleotide building block
<220> FEATURE:
<221> NAME/KEY: misc_feature
<222> LOCATION: (10)..(10)
<223> OTHER INFORMATION: bridged or morpholino nucleotide building block
<220> FEATURE:
<221> NAME/KEY: misc_feature
<222> LOCATION: (15)..(15)
<223> OTHER INFORMATION: bridged or morpholino nucleotide building block
<220> FEATURE:
<221> NAME/KEY: misc_feature
<222> LOCATION: (16)..(16)
<223> OTHER INFORMATION: bridged or morpholino nucleotide building block

<400> SEQUENCE: 2
atggctgtag actgtt                                                    16

<210> SEQ ID NO 3
<211> LENGTH: 16
<212> TYPE: DNA
<213> ORGANISM: Artificial Sequence
<220> FEATURE:
<223> OTHER INFORMATION: oligonucleotide CDR132L
<220> FEATURE:
<221> NAME/KEY: misc_structure
<222> LOCATION: (1)..(1)
<223> OTHER INFORMATION: 2'deoxyadenosine
<220> FEATURE:
<221> NAME/KEY: misc_feature
<222> LOCATION: (1)..(16)
<223> OTHER INFORMATION: phosphorothioate linkage
<220> FEATURE:
<221> NAME/KEY: misc_feature
<222> LOCATION: (2)..(2)
<223> OTHER INFORMATION: LNA building block
<220> FEATURE:
<221> NAME/KEY: misc_structure
<222> LOCATION: (3)..(3)
<223> OTHER INFORMATION: 2'deoxyguanosine
<220> FEATURE:
<221> NAME/KEY: misc_feature
<222> LOCATION: (4)..(4)
<223> OTHER INFORMATION: LNA building block
<220> FEATURE:
<221> NAME/KEY: misc_structure
<222> LOCATION: (5)..(5)
<223> OTHER INFORMATION: 2'deoxycytidine
<220> FEATURE:
<221> NAME/KEY: misc_feature -continued

```
<222> LOCATION: (6)..(6)
<223> OTHER INFORMATION: LNA building block
<220> FEATURE:
<221> NAME/KEY: misc_structure
<222> LOCATION: (7)..(7)
<223> OTHER INFORMATION: 2'deoxyguanosine
<220> FEATURE:
<221> NAME/KEY: misc_feature
<222> LOCATION: (8)..(8)
<223> OTHER INFORMATION: LNA building block
<220> FEATURE:
<221> NAME/KEY: misc_structure
<222> LOCATION: (9)..(9)
<223> OTHER INFORMATION: 2'deoxyadenosine
<220> FEATURE:
<221> NAME/KEY: misc_feature
<222> LOCATION: (10)..(10)
<223> OTHER INFORMATION: LNA building block
<220> FEATURE:
<221> NAME/KEY: misc_structure
<222> LOCATION: (11)..(11)
<223> OTHER INFORMATION: 2'deoxyadenosine
<220> FEATURE:
<221> NAME/KEY: misc_structure
<222> LOCATION: (12)..(12)
<223> OTHER INFORMATION: 2'deoxycytidine
<220> FEATURE:
<221> NAME/KEY: misc_structure
<222> LOCATION: (13)..(13)
<223> OTHER INFORMATION: thymidine
<220> FEATURE:
<221> NAME/KEY: misc_structure
<222> LOCATION: (14)..(14)
<223> OTHER INFORMATION: 2'deoxyguanosine
<220> FEATURE:
<221> NAME/KEY: misc_feature
<222> LOCATION: (15)..(15)
<223> OTHER INFORMATION: LNA building block
<220> FEATURE:
<221> NAME/KEY: misc_feature
<222> LOCATION: (16)..(16)
<223> OTHER INFORMATION: LNA building block

<400> SEQUENCE: 3
atggctgtag actgtt                                                 16
```